US011672787B2

(12) United States Patent
Smeitink et al.

(10) Patent No.: US 11,672,787 B2
(45) Date of Patent: Jun. 13, 2023

(54) COMPOUNDS AS MPGES-1 INHIBITORS

(71) Applicant: Khondrion IP B.V., Beuningen (NL)

(72) Inventors: Johannes Albertus Maria Smeitink, Beuningen (NL); Julien David Beyrath, Nijmegen (NL)

(73) Assignee: Khondrion IP B.V., Beuningen (NL)

( * ) Notice: Subject to any disclaimer, the term of this patent is extended or adjusted under 35 U.S.C. 154(b) by 257 days.

(21) Appl. No.: 16/765,169

(22) PCT Filed: Nov. 22, 2018

(86) PCT No.: PCT/EP2018/082146
§ 371 (c)(1),
(2) Date: May 19, 2020

(87) PCT Pub. No.: WO2019/101826
PCT Pub. Date: May 31, 2019

(65) Prior Publication Data
US 2020/0345706 A1   Nov. 5, 2020

(30) Foreign Application Priority Data
Nov. 22, 2017   (EP) .................... 17203033

(51) Int. Cl.
*A61K 31/439* (2006.01)
*A61K 31/165* (2006.01)
*A61K 31/197* (2006.01)
*A61K 31/355* (2006.01)
*A61K 9/08* (2006.01)

(52) U.S. Cl.
CPC .......... *A61K 31/439* (2013.01); *A61K 31/165* (2013.01); *A61K 31/197* (2013.01); *A61K 31/355* (2013.01); *A61K 9/08* (2013.01)

(58) Field of Classification Search
CPC .. A61K 31/165; A61K 31/197; A61K 31/355; A61K 31/439
See application file for complete search history.

(56) References Cited

U.S. PATENT DOCUMENTS

| | | | | |
|---|---|---|---|---|
| 9,388,156 B2 * | 7/2016 | Blaauw | ................ | C07D 311/66 |
| 9,913,841 B2 * | 3/2018 | Van der Graaf | ..... | A61K 9/0075 |
| 11,285,130 B2 * | 3/2022 | Beyrath | ................ | A61K 31/165 |
| 11,357,767 B2 * | 6/2022 | Smeitink | ................ | A61P 25/06 |

FOREIGN PATENT DOCUMENTS

| | | | |
|---|---|---|---|
| JP | H02250831 A | | 10/1990 |
| JP | 2011503005 A | | 1/2011 |
| JP | 2016511743 A | | 4/2016 |
| WO | WO2006/063466 A1 | | 6/2006 |
| WO | WO2007/059610 A1 | | 5/2007 |
| WO | WO2008/058514 A1 | | 5/2008 |
| WO | WO2008/071173 A1 | | 6/2008 |
| WO | WO2009/130242 A1 | | 10/2009 |
| WO | WO2009/146696 A1 | | 12/2009 |
| WO | WO2010/034796 A1 | | 4/2010 |
| WO | WO2010/100249 A1 | | 9/2010 |
| WO | WO2010/127152 A2 | | 11/2010 |
| WO | WO2012/055995 A1 | | 5/2012 |
| WO | WO2012/076672 A1 | | 6/2012 |
| WO | WO2012/110860 A1 | | 8/2012 |
| WO | WO2013/038308 A1 | | 3/2013 |
| WO | WO2013/072825 A1 | | 5/2013 |
| WO | WO2013/118071 A1 | | 8/2013 |
| WO | WO2013/153535 A1 | | 10/2013 |
| WO | WO2014/011047 A1 | | 1/2014 |
| WO | WO2015/158204 A1 | | 10/2015 |
| WO | WO 2016188766 A1 | | 12/2016 |
| WO | WO2017/060432 A1 | | 4/2017 |

OTHER PUBLICATIONS

Ingold Mariana et al: "A green multicomponent synthesis of tocopherol analogues with antiproliferative activities", European Journal of Medicinal Chemistry, Editions Scientifique Elsevier, Paris, FR, vol. 143, Nov. 3, 2017, pp. 1888-1902.
Koeberle Andreas et al: Perspective of microsomal prostaglandin E2synthase-1 as drug target in inflammation-related disorders, Biochemical Pharmacology, Elsevier, US, vol. 98, No. 1, Jun. 27, 2015, pp. 1-15.
Werz et al: "Inhibitors of the Microsomal Prostaglandin E2 Synthase-1 as Alternative to Non Steroidal Anti-Inflammatory Drugs (NSAIDs)—A Critical Review", Current Medicinal Chemistry : The New International Journal for Timely In-Depth Reviews in Medicinal Chemistry, Bentham,A 1-14 NL, vol. 16, No. 32, Nov. 1, 2009, pp. 4274-4296.
Sasaki Yuka et al: Role of microsomal prostaglandin E synthase-1 (mPGES-1)-derived prostaglandin E2in colon carcinogenesis, Prostaglandins and Other Lipid Mediators, vol. 121, Jul. 3, 2015 (Jul. 3, 2015), pp. 42-45. Beales, I.L.P., and Ogunwobi, O.O. (2010). Microsomal prostaglandin E synthase-1 inhibition blocks proliferation and enhances apoptosis in oesophageal adenocarcinoma cells without affecting endothelial prostacyclin production. Int. J. Cancer 126: 2247-55.
Chaudhry, U.A., Zhuang, H., Crain, B.J., and Doré, S. (2008). Elevated microsomal prostaglandin-E synthase-1 in Alzheimer's disease. Alzheimer's Dement. 4: 6-13.
Chen, Y., Liu, H., Xu, S., Wang, T., and Li, W. (2015). Targeting microsomal prostaglandin E 2 synthase-1 (mPGES-1) the development of inhibitors as an alternative to non-steroidal anti-inflammatory drugs (NSAIDs). Med. Chem. Commun. 6: 2081-2123.

(Continued)

*Primary Examiner* — James D. Anderson
(74) *Attorney, Agent, or Firm* — N.V. Nederlandsch Octrooibureau

(57) ABSTRACT

The invention relates to amide-derivatives of 2-hydroxy-2-methyl-4-(3,5,6-trimethyl-1,4-benzoquinon-2-yl)-butanoic acid for use in a treatment for preventing or suppressing symptoms mediated by enhanced mPGES-1 expression or activity. In particular the invention relates the use of these compounds for treating diseases and conditions in which the inhibition of the enzyme mPGES-1 activity and/or expression would be beneficial such as inflammatory diseases, nociceptive pain, auto-immune diseases, breathing disorders, fever, cancer, inflammation related anorexia, Alzheimer's disease and cardiovascular disease.

17 Claims, 11 Drawing Sheets
Specification includes a Sequence Listing.

(56) References Cited

OTHER PUBLICATIONS

Fahmi, H. (2004). mPGES-1 as a novel target for arthritis. Curr. Opin. Rheumatol. 16: 623-627.

Hanaka, H., Pawelzik, S.-C., Johnsen, J.I., Rakonjac, M., Terawaki, K., Rasmuson, A., et al. (2009). Microsomal prostaglandin E synthase 1 determines tumor growth in vivo of prostate and lung cancer cells. Proc. Natl. Acad. Sci. U. S. A. 106: 18757-62.

Hara, S., Kamei, D., Sasaki, Y., Tanemoto, A., and Nakatani, Y. (2010). Prostaglandin E synthases: Understanding their pathophysiological roles through mouse genetic models. Biochimie 92: 651-659.

Ikeda-Matsuo, Y. (2017). The Role of mPGES-1 in Inflammatory Brain Diseases. Biol. Pharm. Bull 40: 557-563.

Ikeda-Matsuo, Y., Ikegaya, Y., Matsuki, N., Uematsu, S., Akira, S., and Sasaki, Y. (2005). Microglia-specific expression of microsomal prostaglandin E2 synthase-1 contributes to lipopolysaccharide-induced prostaglandin E2 production. J. Neurochem. 94: 1546-1558.

Kamei, D., Yamakawa, K., Takegoshi, Y., Mikami-Nakanishi, M., Nakatani, Y., Oh-Ishi, S., et al. (2004). Reduced pain hypersensitivity and inflammation in mice lacking microsomal prostaglandin e synthase-1. J. Biol. Chem. 279: 33684-95.

Kats, A., Båge, T., Georgsson, P., Jönsson, J., Quezada, H.C., Gustafsson, A., et al. (2013). Inhibition of microsomal prostaglandin E synthase-1 by aminothiazoles decreases prostaglandin E2 synthesis in vitro and ameliorates experimental periodontitis in vivo. FASEB J. 27: 2328-41.

Kim, S.-H., Hashimoto, Y., Cho, S.-N., Roszik, J., Milton, D.R., Dal, F., et al. (2016). Microsomal PGE2 synthase-1 regulates melanoma cell survival and associates with melanoma disease progression. Pigment Cell Melanoma Res. 29: 297-308.

Larsson, K., and Jakobsson, J. (2015). Inhibition of microsomal prostaglandin E synthase-1 as targeted therapy in cancer treatment. Prostaglandins Other Lipid Mediat. 120:161-165.

Mcadam, B.F., Catella-Lawson, F., Mardini, I.A., Kapoor, S., Lawson, J.A., and Fitzgerald, G.A. (1999). Systemic biosynthesis of prostacyclin by cyclooxygenase (COX)-2: The human pharmacology of a selective inhibitor of COX-2 (prostaglandins/platelets/monocytes/ibuprofen/celecoxib). Pharmacology 96:272-277.

Miller, S.B. (2006). Prostaglandins in Health and Disease: An Overview. Semin. Arthritis Rheum. 36: 37-49.

Miyagishi, H., Kosuge, Y., Ishige, K., and Ito, Y. (2012). Expression of microsomal prostaglandin E synthase-1 in the spinal cord in a transgenic mouse model of amyotrophic lateral sclerosis. J. Pharmacol. Sci. 118: 225-36.

Nakanishi, M., Gokhale, V., Meuillet, E.J., and Rosenberg, D.W. (2010). mPGES-1 as a target for cancer suppression: A comprehensive invited review "Phospholipase A2 and lipid mediators ". Biochimie 92: 660-4.

Nakanishi, M., and Rosenberg, D.W. (2013). Multifaceted roles of PGE2 in inflammation and cancer. Semin. Immunopathol. 35: 123-137.

Norberg, J.K., Sells, E., Chang, H.-H., Alla, S.R., Zhang, S., and Meuillet, E.J. (2013a). Targeting inflammation: multiple innovative ways to reduce prostaglandin $E_2$. Pharm. Pat. Anal. 2: 265-88.

Norberg, J.K., Sells, E., Chang, H , Alla, S.R., Zhang, S., and Meuillet, E.J. (2013b). Targeting inflammation: multiple innovative ways to reduce prostaglandin $E_2$. Pharm. Pat. Anal. 2: 265-88.

Ricciotti, E., and FitzGerald, G.A. (2011). Prostaglandins and inflammation. Arterioscler. Thromb. Vasc. Biol. 31: 986-1000.

Riendeau, D., Aspiotis, R., Ethier, D., Gareau, Y., Grimm, E.L., Guay, J., et al. (2005). Inhibitors of the inducible microsomal prostaglandin E2 synthase (mPGES-1) derived from MK-886. Bioorg. Med. Chem. Lett. 15: 3352-3355.

Samuelsson, B., Morgenstern, R., and Jakobsson, P.-J. (2007). Membrane Prostaglandin E Synthase-1: A Novel Therapeutic Target. Pharmacol. Rev. Pharmacol Rev 59: 207-224.

Smith, W.L., Urade, Y., and Jakobsson, P.-J. (2011). Enzymes of the Cyclooxygenase Pathways of Prostanoid Biosynthesis. 111: 5821-5865.

Takeuchi, C., Matsumoto, Y., Kohyama, K., Uematsu, S., Akira, S., Yamagata, K., et al. (2013). Microsomal prostaglandin E synthase-1 aggravates inflammation and demyelination in a mouse model of multiple sclerosis. Neurochem. Int. 62: 271-80.

Westman, M., Korotkova, M., Klint, E. af, Stark, A., Audoly, L.P., Klareskog, L., et al. (2004). Expression of microsomal prostaglandin E synthase 1 in rheumatoid arthritis synovium. Arthritis Rheum. 50: 1774-1780.

Zeilhofer, H.U. (2007). Prostanoids in nociception and pain. Biochem. Pharmacol. 73: 165-174.

Catella-Lawson, Francesca, et al. "Effects of specific inhibition of cyclooxygenase-2 on sodium balance, hemodynamics, and vasoactive eicosanoids." Journal of Pharmacology and Experimental Therapeutics 289.2 (1999): 735-741.

Hui, Yiqun, et al. "Targeted deletions of cyclooxygenase-2 and atherogenesis in mice." Circulation 121.24 (2010): 2654-2660.

Larsson, Karin, et al. "COX/mPGES-1/PGE2 pathway depicts an inflammatory-dependent high-risk neuroblastoma subset." Proceedings of the National Academy of Sciences 112.26 (2015): 8070-8075.

Seo, Tsuguhiko, et al. "Microsomal prostaglandin E synthase protein levels correlate with prognosis in colorectal cancer patients." Virchows Archiv 454.6 (2009): 667-676.

Yoshimatsu, Kazuhiko, et al. "Inducible prostaglandin E synthase is overexpressed in non-small cell lung cancer." Clinical Cancer Research 7.9 (2001): 2669-2674.

Armstrong, D. ed., 2010. Advanced protocols in oxidative stress II (vol. 28). Totowa, NJ, USA:: Humana Press.

\* cited by examiner

US 11,672,787 B2

COMPOUNDS AS MPGES-1 INHIBITORS

FIELD OF THE INVENTION

The present invention relates to the fields of human and veterinary medicine and cosmetics. The invention in particular relates to amide-derivatives of 2-hydroxy-2-methyl-4-(3,5,6-trimethyl-1,4-benzoquinon-2-yl)-butanoic acid for treating conditions in which the inhibition of the enzyme mPGES-1 activity and/or expression would be beneficial such as inflammatory diseases, nociceptive pain, auto-immune diseases, breathing disorders, fever, cancer, inflammation related anorexia, Alzheimer's disease and cardiovascular disease.

BACKGROUND ART

Prostaglandins (PG) are important lipid mediators sustaining physiological and homeostatic functions but also inducing pathologic response such as inflammatory and nociceptive responses (Miller, 2006). Prostaglandins are synthesized from arachidonic acid (AA) which is released from the cell membrane by the action of phospholipase A2 ($PLA_2$). Cyclooxygenases isoforms 1 and 2 (COX-1 and COX-2) enzymes metabolize AA into prostaglandin $G_2$ ($PGG_2$) and subsequently to prostaglandin $H_2$ ($PGH_2$) by bis-oxygenation and peroxidation reaction, respectively. $PGH_2$ is the common precursor of the four principal bioactive prostaglandins $PGD_2$, $PGI_2$, $PGE_2$ and $PGF_{2\alpha}$ and the prostanoid thromboxane $A_2$ ($TXA_2$) that are synthesized by cell- and tissue-specific synthases and isomerases (FIG. 1). Prostaglandins play a key role in the generation of the inflammatory response (Ricciotti and FitzGerald, 2011). Their biosynthesis is significantly increased in inflamed tissue and they contribute to the development of the cardinal signs of acute inflammation. Among the prostanoids, $PGE_2$ has the greatest impact on processing of inflammatory pain signals (Nakanishi and Rosenberg, 2013). PGE2 is synthesized by three different $PGE_2$ synthases which are either membranous enzymes (mPGES-1, mPGES-2) or cytosolic (cPGES) (Nara et al., 2010). Of these PGE synthases, cPGES and mPGES-2 are constitutively expressed in various organs and tissues, whereas mPGES-1, like COX-2, is up-regulated in response to various inflammatory stimuli (Ikeda-Matsuo et al., 2005; Riendeau et al., 2005; Smith et al., 2011). Following inflammation or nociception triggers, mPGES-1 and COX-2 are induced in the peripheral (PNS) and central nervous system (CNS) where they contribute to the generation of $PGE_2$ and the development of chronic pain (Zeilhofer, 2007). Current Non-Steroidal Anti-Inflammatory Drugs (NSAIDs) target the upstream COX enzymes in the synthesis of prostaglandins. COX-1/2 non-selective inhibitors or COX-2 selective inhibitors (Coxibs) are the most commonly prescribed medications for inflammatory pain indications. Both classes of NSAIDs have been associated with serious cardiovascular and gastrointestinal adverse events (Norberg et al., 2013a). COX-1 enzyme is constitutively expressed in most tissues and has a gastro-protective action; therefore, COX-1 inhibitors can induce gastric damages. Despite being mainly expressed in inflamed tissues, COX-2 selective inhibitors have been linked to cardiovascular adverse effects and hypertension. Research has shown that those effects were attributed to the suppression of COX-2-mediated prostacyclin ($PGI_2$) synthesis (Catella-Lawson et al.; Mcadam et al., 1999; Hui et al., 2010). Indeed, $PGI_2$ plays an important role in the dilatation of blood vessels, the inhibition of platelet-aggregation, and is cardio protective. mPGES-1 is strongly up-regulated by inflammatory stimuli and contributing to the production of pro-inflammatory, pro-nociceptive and proangiogenic $PGE_2$. Targeting downstream enzyme mPGES-1 has recently appeared as a safer alternative than current classes of NSAIDs or Coxibs (Samuelsson et al., 2007; Koeberle and Werz, 2009, 2015a; Chen et al., 2015). Indeed, contrarily to its upstream enzymes COX-1 and COX-2, inhibition of mPGES-1 selectively blocks inflammation-inducible $PGE_2$ without reducing the synthesis and function of other prostaglandins. Targeting mPGES-1 would therefore reduce the adverse effects imputable to the non-selective inhibition of prostaglandins synthesis by NSAIDs or to the inhibition of COX-1 itself (Norberg et al., 2013b; Koeberle and Werz, 2015b). mPGES-1 is weakly expressed in normal tissues and upregulated in inflamed tissues, therefore less prone to on-target adverse effects. Engineered mice lacking mPGES-1 are viable and do not exhibit any abnormal phenotype. They were shown to have reduced symptoms associated with inflammation, such as swelling, anorexia or fever, and also a reduced sensitivity to pain (Kamei et al., 2004; Hara et al., 2010). These data corroborate the validity of mPGES-1 as a drug target for inflammatory-related disease. In addition, its expression has been reported to be over-expressed in inflamed tissues of patients suffering from, but not limited to, arthritis, gout, bowel disease, and periodontitis and patients with neuro-inflammation such as Alzheimer's disease, Amyotrophic Lateral Sclerosis, Parkinson's disease, brain ischemia, epilepsy, brain cancer and multiple sclerosis (Fahmi, 2004; Westman et al., 2004; Kojima et al., 2005; Chaudhry et al., 2008; Miyagishi et al., 2012; Akitake et al., 2013; Kats et al., 2013; Takeuchi et al., 2013; Ikeda-Matsuo, 2017). mPGES-1 is also over-expressed in numerous cancers and its inhibition has been reported to be an effective treatment for cancer in various pre-clinical models (Larsson et al.; Seo et al.; Yoshimatsu et al.; Hanaka et al., 2009; Beales and Ogunwobi, 2010; Nakanishi et al., 2010; Larsson and Jakobsson, 2015; Sasaki et al., 2015; Kim et al., 2016; Ramanan and Doble, 2017). Overall, mPGES-1 and mPGES-1-derived PGE2 have been ascribed to a role in the patho-mechanisms of large panel of diseases and conditions inflammatory diseases, nociceptive pain, auto-immune diseases, breathing disorders, fever, cancer, inflammation related anorexia, Alzheimer's disease and cardiovascular disease. Inhibitors of mPGES-1 therefore represent an effective option for the treatment of all above mentioned diseases and conditions.

WO 2006/063466, WO 2007/059610, WO 2008/058514, WO 2008/071173, WO 2009/130242, WO 2009/146696, WO 2010/034796, WO 2010/100249, WO 2010/127152, WO 2011/023812 WO 2012/055995, WO 2012/076672, WO 2012/110860, WO 2013/038308 WO 2013/072825, WO 2013/118071, WO 2013/153535 and WO 2015/158204 disclose numerous compounds which are stated to be inhibitors of mPGES-1.

WO2014/011047 and WO2017/060432 disclose amide-derivatives of 2-hydroxy-2-methyl-4-(3,5,6-trimethyl-1,4-benzoquinon-2-yl)-butanoic acid for treating or preventing mitochondrial disorders and/or conditions associated with mitochondrial dysfunction.

There is however still a need in the art for further mPGES-1-inhibiting compounds that have improved safety, efficacy and/or (oral) bioavailability profiles. The present application is directed to such further compounds that act as inhibitors of mPGES-1 and, therefore, are useful for the treatment of conditions in which the inhibition of the enzyme mPGES-1 activity and/or expression would be beneficial, including e.g. the prevention or suppression of inflammation and pain in a variety of diseases or conditions.

SUMMARY OF THE INVENTION

In a first aspect, the invention relates to a compound represented by general structure (I):

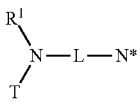
(I)

wherein,
- T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;
- L is a linker between the amide nitrogen atom and the distal nitrogen atom comprising 1 to 10 optionally substituted backbone atoms selected from carbon, nitrogen and oxygen;
- N* is represented by structure (IIa) or (IIb)

(IIa)

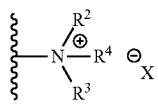
(IIb)

- $R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; and
- $R^4$ is selected from hydrogen (H) or $C_1$-$C_6$ alkyl, wherein the alkyl moiety may be substituted with one or more halogen atoms or (halo)alkoxy moieties;
- X is an anion, preferably a pharmaceutically acceptable anion, for use in a treatment for preventing or suppressing symptoms mediated by enhanced mPGES-1 expression or activity.

In particular embodiments of this aspect, the invention provides the compound for use according to the invention, wherein the compound is represented by structure (VI):

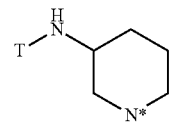
(VI)

wherein N* is —$NR^3$ or —$N^+R^3R^4X^-$, wherein T, X, $R^3$, and $R^4$ are as defined above.

In preferred embodiments of this aspect, the invention provides a compound for use according to the invention, wherein T is represented by structure (IIIa) or (IIIb):

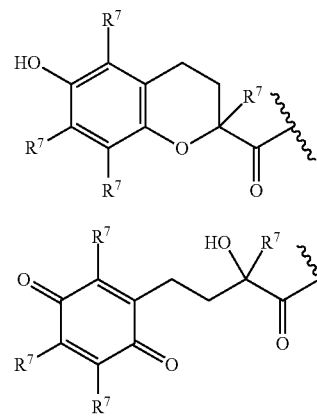
(IIIa)

(IIIb)

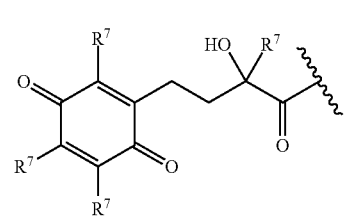

wherein each $R^7$ is individually a $C_1$-$C_6$ alkyl moiety, preferably each $R^7$ is methyl.

In preferred embodiments of this aspect, the invention provides a compound for use according to the invention, wherein the compound is represented by structure (VIIb):

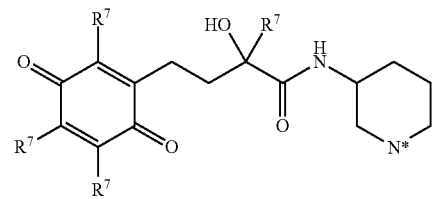
(VIIb)

wherein
- each $R^7$ is methyl;
- N* is —$NR^3$ or —$N^+R^3R^4X^-$;
- X is as defined above and is preferably $Cl^-$;
- $R^3$ is as defined above and is preferably hydrogen; and
- $R^4$ is as defined above and is preferably hydrogen.

In preferred embodiments of this aspect, the invention provides a compound for use according to the invention, wherein the symptoms mediated by enhanced mPGES-1 expression or activity at least include one or more of inflammation, pain, swelling, fever, angiogenesis and anorexia. Preferably, the compound is used for preventing or suppressing symptoms mediated by enhanced mPGES-1 expression or activity in the treatment of a disease or condition selected from the group consisting of:

a) acute and chronic inflammation; skin diseases such as dermatitis, eczema, psoriasis, burns, acne vulgaris, hidradenitis suppurativa and tissue trauma; visceral diseases such as inflammatory bowel disease, Crohn's disease, ulcerative colitis, diverticulitis, irritable bowel disease (IBS), peptic ulcers, cystitis, (chronic) prostatitis, pancreatitis or nephritis; ear, nose, mouth and throat disease such as influenza, rhinitis, pharyngitis, tonsillitis, conjunctivitis, iritis, scleritis, otitis and uveitis; viral and bacterial infections; inflammation related anorexia; an allergy; pelvic inflammatory disease; reperfusion injury; transplant rejection; tendinitis, vasculitis and phlebitis;

b) acute pain, chronic pain, neuropathic pain, nociceptive pain, hyperalgesia, pain related to central sensitization, allodynia inflammatory pain, visceral pain, cancer pain, trauma pain, dental or surgery pain, postoperative pain, delivery pain, childbirth ache, persistent pain, peripheral mediated pain, central mediated pain, chronic headache, migraine, sinus headaches, tension headaches, phantom limb pain, peripheral nerve injury chemotherapy pain, and cancer pain;

c) an autoimmune disease such as arthritis, osteoarthritis, juvenile arthritis, rheumatoid arthritis, ankylosing spondylitis, gout, rheumatic fever, bursitis, systemic lupus erythematosus (SLE) and multiple sclerosis;

d) a breathing disorder or lung disease such as asthma, chronic obstructive pulmonary disease (COPD), sarcoidosis and pulmonary fibrosis;

e) a cancer such as brain cancer, prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma and skin B-cell lymphoma;

f) diabetic complications include diabetic vasculopathy, diabetic neuropathy and diabetic retinopathy;

g) a neurodegenerative disorder such as Alzheimer's disease, Parkinson's disease, Huntington's disease and amyotrophic lateral sclerosis; and, h) a cardiovascular disease such as atherosclerosis, thrombosis, stroke and coronary heart disease.

In preferred embodiments of this aspect, the invention provides a compound for use according to the invention, wherein the total daily dose that is administered is in the range of about 5 to 2000 mg, preferably about 20 to 800 mg, more preferably the total daily dose is in the range of between about 30 to 400 mg and most preferably the total daily dose is in the range of about 150 to 250 mg. Preferably the compound is administered orally. Preferably, the compound is administered in a solid form or in a liquid form, wherein preferably the compound is admixed with an aqueous solution prior to administration, wherein more preferably the aqueous solution is an isotonic aqueous solution and wherein even more preferably the isotonic aqueous solution is saline. Preferably, the compound is administered at least twice daily, preferably wherein the compound is administered twice daily, wherein more preferably the compound is administered twice daily in two similar or equal doses. Preferably, the interval between two administrations is at least about 1, 2, 3, 4, 5, 6, 7, 8, 9, 10, 11 or 12 hours. Preferably, the subject to be treated is a primate, wherein more preferably the subject is a human.

In a second aspect, the invention provides a method for treating a disease or condition mediated by or associated with enhanced mPGES-1 expression or activity, wherein the method comprises the step of administering to a subject suffering from the disease or condition an effective amount of a compound as defined above.

In preferred embodiments of this aspect, the invention provides the method as described above, wherein the disease or condition mediated by or associated with enhanced mPGES-1 expression or activity preferably is selected from the group consisting of a) acute and chronic inflammation; skin diseases such as dermatitis, eczema, burns, acne vulgaris, hidradenitis suppurativa and tissue trauma; visceral diseases such as ulcerative colitis, diverticulitis, irritable bowel disease (IBS), peptic ulcers, cystitis, (chronic) prostatitis or nephritis; ear, nose, mouth and throat disease such as influenza, rhinitis, pharyngitis, tonsillitis, conjunctivitis, iritis, scleritis, otitis and uveitis; viral and bacterial infections; inflammation related anorexia; an allergy; pelvic inflammatory disease; transplant rejection; tendinitis, vasculitis and phlebitis; b) acute pain, chronic pain, neuropathic pain, nociceptive pain, hyperalgesia, pain related to central sensitization, allodynia inflammatory pain, visceral pain, cancer pain, trauma pain, dental or surgery pain, postoperative pain, delivery pain, childbirth ache, persistent pain, peripheral mediated pain, central mediated pain, chronic headache, migraine, sinus headaches, tension headaches, phantom limb pain, peripheral nerve injury chemotherapy pain, and cancer pain; c) ankylosing spondylitis, gout, rheumatic fever, bursitis; and d) diabetic complications include diabetic vasculopathy, diabetic neuropathy and diabetic retinopathy.

DESCRIPTION OF THE INVENTION

The current invention pertains to the discovery that compounds of the invention, such as amide-derivatives of 2-hydroxy-2-methyl-4-(3,5,6-trimethyl-1,4-benzoquinon-2-yl)-butanoic acid, are able to effectively and selectively reduce the level of mPGES-1-induced $PGE_2$, without affecting the level of other prostaglandins by blocking the expression of mPGES-1 and its enzymatic activity. The compounds are therefore useful in treatments for preventing or suppressing symptoms mediated by enhanced mPGES-1 expression or activity and/or mediated by the (resulting) increased levels of $PGE_2$.

In a first aspect, the invention therefore concerns a method of treating, preventing, or suppressing symptoms mediated by enhanced mPGES-1 expression or activity, the method comprising administering to a subject in need thereof, an effective amount of one or more compounds of the invention as defined herein below. The effective amount is preferably an amount as defined herein below.

Alternatively, the invention pertains to a compound of the invention as defined herein below for use in treating, preventing, or suppressing symptoms mediated by enhanced mPGES-1 expression or activity, preferably by administration of an effective dose of the compound as defined herein below.

The medical use herein described is formulated as a compound as defined herein for use as a medicament for treatment of the stated condition(s) (e.g. by administration of an effective amount of the compound), but could equally be formulated as i) a method of treatment of the stated condition(s) using a compound as defined herein comprising a step of administering to a subject an effective amount of the compound, ii) a compound as defined herein for use in the manufacture of a medicament to treat the stated condition(s), wherein preferably the compound is to be administered in an effective amount, and iii) use of a compound as defined herein for the treatment of the stated condition(s), preferably by administering an effective amount. Such medical uses are all envisaged by the present invention.

The compound of the invention may be identified by general structure (I):

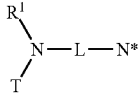
(I)

Herein,
T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;
L is a linker between the amide nitrogen atom and the distal nitrogen atom comprising 1 to 10 optionally substituted backbone atoms selected from carbon, nitrogen and oxygen;
N* is represented by structure (IIa) or (IIb)

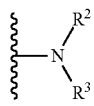
(IIa)

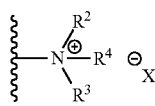
(IIb)

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with a backbone atom of the linker L in a cyclic structure; and
$R^4$ is selected from hydrogen (H) or $C_1$-$C_6$ alkyl, wherein the alkyl moiety may be substituted with one or more halogen atoms or (halo)alkoxy moieties;
X is an anion, preferably a pharmaceutically acceptable anion.

The compound according to structure (I) comprises at least two nitrogen atoms; the nitrogen atom to which T is connected, which is also referred to as the "amide nitrogen atom", and the nitrogen atom of the N* moiety, which is also referred to as the "distal nitrogen atom". N* may be an amino moiety, when the covalent bond between the distal nitrogen atom and the adjacent backbone atom is a single bond, or part of an imine moiety, when the covalent bond between the distal nitrogen atom and adjacent backbone atom is a double bond. The distal nitrogen atom may be a neutral or a cationic. In case N* is neutral, the compound according to the invention may also be referred to by general structure (Ia). In case N* is cationic, the compound according to the invention may also be referred to by general structure (Ib).

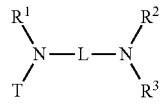
(Ia)

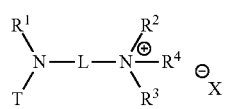
(Ib)

T is a water-soluble vitamin E derivative, wherein the chromanyl or chromanyl quinone framework is substituted with a carboxylic acid at the 2-position. The 2-carboxy variant of vitamin E is also known as Trolox™ (6-hydroxy-2,5,7,8-tetramethylchroman-2-carboxylic acid). Water-soluble vitamin E derivatives are known in the art and include 6-hydroxy-2,5,7,8-tetraalkyl-2-carboxy-chromanyl (general structure (IIIa), also referred to as the "closed form") and its oxidized form 2-(3-hydroxy-3-alkyl-4-oxobutyl)-3,5,6-trialkylcyclohexa-2,5-diene-1,4-dione (general structure (IIIb), also referred to as the "open form"). The inventors have found that the open form according to general structure (IIIb) is found as metabolite of the closed form according to general structure (IIIa), when the latter is administered. After 24 h treatment of a P4 cell line with compound I-IVa-X (a compound of general structure (I) wherein T is of general structure (IVa), in the S,R-configuration, and wherein as per compound X the following apply: $L=L^{19}$; $R^1$=H; $R^2$—$R^{2'}$=$L^3$; $R^3$=H), about 48% (±10%) of closed compound was converted into the open form. About 15% (±3%) was converted during the same period when incubated in medium only. Such conversion is also disclosed in Beyrath et al., DOI: 10.1038/s41598-018-24900-3, and in Koene et al., DOI: 10.1186/s13023-017-0715-0. A preferred chromanyl framework is a 6-hydroxychromane framework. A preferred chromanyl quinone framework is a 2-(3-hydroxyalkyl)-cyclohexa-2,5-diene-1,4-dione, wherein preferably a 3-hydroxyalkyl is a 3-hydroxybutyl, more preferably a 4-oxo-3-hydroxybutyl as comprised in general structure (IIIb).

The 2-position of the closed form is the position in the oxane ring bearing the carboxylic acid (or amide, as is the case in a molecule of the invention) and an $R^7$ moiety, which is the 2-position according to naming conventions known in the art, such as IUPAC nomenclature. For the open form, the same carbon atom is intended with the 2-position, so that the carbon atom bearing the hydroxyl moiety and an R7 moiety such as shown in general structure (IIIb) below is referenced. This position can also be seen as the 3-position of the alkyl moiety that is substituted to the quinone. Accordingly, T is a water-soluble vitamin E derivative, wherein the chromanyl framework is substituted with a carboxylic acid at the 2-position or wherein the chromanyl quinone framework is substituted with a carboxylic acid at the 3-position of the 3-hydroxyalkyl moiety, which is in turn substituted to the 2'position of the cyclohexa-2,5-diene-1,4-dione.

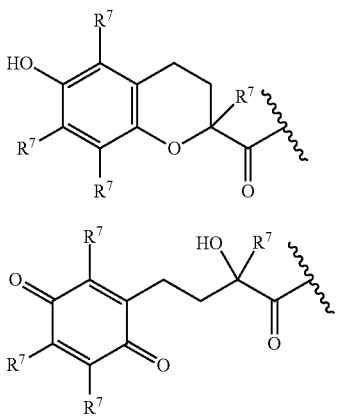

(IVa)

(IVb)

Herein, each occurrence of $R^7$ is individually selected from halogen, alkyl, amino, nitro or —NHCO-alkyl. Preferred options for $R^7$ are halogen and alkyl, most preferably alkyl. In the context of $R^7$, the halogen is preferably fluorine or chlorine, most preferably chlorine. In the context of the alkyl is preferably a $C_1$-$C_6$ alkyl moiety, preferably a $C_1$-$C_6$ alkyl moiety, most preferably methyl. In the context of $R^7$, amino is preferably —$NH_2$. In the context of $R^7$, —NHCO-alkyl is preferably —NHCOMe. Preferably, each of $R^7$ is the same substituent. Most preferably, $R^7$ is methyl. In a preferred embodiment, T is represented by structure (IVa) or (IVb). In other words, structure (IVa) is a preferred embodiment of structure (IIIa), and structure (IVb) is a preferred embodiment of structure (IIIb).

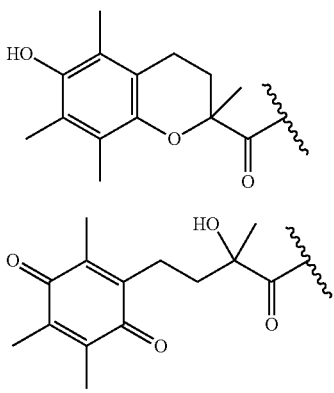

(IVa)

(IVb)

In a preferred embodiment, T is represented by structure IIIa or IIIb, preferably by structure IVa or IVb. In a more preferred embodiment, T is represented by structure (IIIa), preferably by structure (IVa). In an even more preferred embodiment, T is represented by structure (IIIb), preferably by structure (IVb).

The compound identified by general structure (I) comprises at least one chiral carbon atom (stereocenter), i.e. the atom at the 2-position of T (e.g. of the oxane ring of structure (IIIa) or the butanoic acid moiety of structure (IIIa)). Both the compound having an S-configuration as the compound having an R-configuration of the carbon atom at the 2-position are encompassed in the present invention, as well as mixtures of the different stereoisomers. Such a mixture may have one of the configurations in enantiomeric excess, or may be racemic. Whenever one or more additional stereocenters are present in the compound according to the invention, for example in linker L, each may individually exist in the S-configuration, in the R-configuration, or as a mixture of both configurations. Such a mixture may have one of the configurations in enantiomeric excess, or may be racemic. In case addition stereocenters are present, all diastereomers of the compound of general structure (I), in each possible ratio, are encompassed in the present invention.

In a preferred embodiment, the solubility of the compound of the invention in water, expressed as $\log(P_{ow})$ is between 2.0 and 5.0, preferably between 2.5 and 4.5, more preferably between 3.0 and 4.0. $\log(P_{ow})$, the logarithm of the partition coefficient between 1-octanol and water, is a well-known measure of water solubility. Compounds having a $\log(P_{ow})$ value between 3 and 4 are ideally balanced between sufficient water solubility for preparation of aqueous solutions or suspensions and sufficient lipophilicity to ensure efficient transport of the compound over the cellular membrane. The skilled person will appreciate how to determine which combinations of L, $R^1$, $R^2$, $R^3$, $R^4$ and X as defined herein to afford a compound having a $\log(P_{ow})$ value between 3 and 4. Suitable tests to define the $\log(P_{ow})$ value of a compound are well-known to the skilled person, and include but are not limited to the shake-flask method, ITIES, the droplet method or using HPLC. The $\log(P_{ow})$ of a compound can also be predicted using QSPR algorithms.

$R^1$ and $R^2$ are each independently selected from hydrogen (H), $C_1$-$C_6$ alkyl or $C_1$-$C_6$ alkenyl, or one or both of $R^1$ and $R^2$ are embedded in a cyclic structure as described here below. Preferably, $R^1$ is H or $C_1$-$C_2$ alkyl or $R^1$ and $R^2$ are joined together and thus form a second linker between the amide nitrogen atom and the distal nitrogen atom, or $R^1$ is joined with a backbone atom of the linker L in a cyclic structure, more preferably $R^1$ is H or $C_1$-$C_2$ alkyl, even more preferably $R^1$ is H or methyl (Me), most preferably $R^1$ is H. Preferably, $R^2$ is H or $C_1$-$C_2$ alkyl or $R^1$ and $R^2$ are joined together and thus form a second linker between the amide nitrogen atom and the distal nitrogen atom, or $R^2$ is joined with a backbone atom of the linker L in a cyclic structure, more preferably $R^2$ is H, $C_1$-$C_2$ alkyl or joined with a backbone atom of the linker L in a cyclic structure, even more preferably $R^2$ is H, methyl (Me) or joined with a backbone atom of the linker L in a cyclic structure. In one embodiment, $R^2$ is H, methyl (Me), preferably $R^2$ is H. In an especially preferred embodiment, $R^2$ is joined with a backbone atom of the linker L in a cyclic structure, as further defined below, preferably a saturated cyclic structure, most preferably a piperidine ring.

In one embodiment, the amide nitrogen atom is connected to the distal nitrogen atom via a second linker. This second linker is defined by joining together $R^1$ on the amide nitrogen atom and $R^2$ on the distal nitrogen atom. Thus, the amide nitrogen atom, the distal nitrogen atom, the first linker and the second linker together form a cyclic structure, preferably a 4-10-membered cyclic structure, more preferably a 5-8-membered cyclic structure, most preferably a 6-membered cyclic structure. In a preferred embodiment, the second linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the distal nitrogen atom.

In another embodiment, the amide nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{1'}$, which is joined together with $R^1$ on the amide nitrogen atom. Thus, the amide nitrogen atom, part of first linker located between the amide nitrogen atom and the atom bearing $R^{1'}$, the backbone atom bearing $R^{1'}$ and the second linker together form the cyclic structure. In this embodiment, the distal nitrogen atom is not included in this cyclic structure, but instead only part of the backbone of the linker is included. In a preferred embodiment, this connection between the amide nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the backbone atom of the linker. Most preferably, the cyclic structure containing the amide nitrogen atom is a fully saturated ring, preferably selected from a piperidine ring, a pyrrolidine ring, a piperazine ring, an imidazolidine ring, a pyrazolidine ring and an azepane ring, more preferably a piperazine ring, a piperidine ring or a pyrrolidine ring, most preferably a piperidine ring.

In another embodiment, the distal nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{2'}$, which is joined together with $R^2$ on the distal nitrogen atom. Thus, the distal nitrogen atom, part of first linker located between the distal nitrogen atom and the atom bearing $R^{2'}$, the backbone atom bearing $R^{2'}$ and the second linker together form the cyclic structure. In this embodiment, the amide nitrogen atom is not included in this cyclic structure, but instead only part of the backbone of the linker is included. In a preferred embodiment, this connection between the distal nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the distal nitrogen atom and the backbone atom of the linker. Most preferably, the cyclic structure containing the distal nitrogen atom is a fully saturated ring, preferably selected from a piperidine ring, a pyrrolidine ring, a piperazine ring, an imidazolidine ring, a pyrazolidine ring and an azepane ring, more preferably a piperidine ring or a pyrrolidine ring, most preferably a piperidine ring. It is also possible that a connection exists between $R^1$ on the amide nitrogen atom and an $R^{1'}$ substituent on the linker and between $R^2$ on the distal nitrogen atom and an $R^{2'}$ substituent on the linker.

In another embodiment, the distal nitrogen atom is connected to a backbone atom of the linker via a second and a third linker, thereby forming a bicyclic structure, preferably a 6-12-membered cyclic structure, more preferably a 6-9-membered cyclic structure such as a bicyclooctane-like structure, most preferably a [2.2.2]bicyclooctane-like structure. The backbone atom of the linker to which the nitrogen atom is connected in this respect has a substituent $R^{2'}$ and $R^{3'}$ which are joined together with $R^2$ and $R^3$, respectively, on the distal nitrogen atom. Thus, the distal nitrogen atom, part of first linker located between the distal nitrogen atom and the atom bearing $R^{2'}$, the backbone atom bearing $R^{2'}$ and the second linker together form one cycle of the bicyclic structure, and the part of the first linker located between the distal nitrogen atom and the atom bearing R3', and the third linker form a second cycle of the bicyclic structure. In this embodiment, the amide nitrogen atom is not included in this bicyclic structure, but instead only part of the backbone of the linker is included. In a preferred embodiment, this connection between the distal nitrogen atom and a backbone atom of the linker is a —$CH_2$—, —$CH_2$—$CH_2$— or —$CH_2$—$CH_2$—$CH_2$— bridge, most preferably a —$CH_2$—$CH_2$— bridge, wherein two or three, preferably two, carbon atoms are present between the distal nitrogen atom and the backbone atom of the linker. Most preferably, the cyclic structure containing the distal nitrogen atom is a fully saturated structure.

Among the above-mentioned possibilities for $R^2$, it is most preferred that the distal nitrogen atom is connected to a backbone atom of the linker via a second linker wherein $R^2$ is joined with $R^{2'}$, as further defined here above.

When the distal nitrogen atom is part of an imine moiety, the linker L comprises at least one double bond located between the distal nitrogen atom and the adjacent backbone atom of the linker, or $R^2$ comprises at least one double bond located between the distal nitrogen atom and the adjacent atom of $R^2$ (i.e. $R^2$=$C_1$-$C_8$ alkenyl). In such instances, $R^3$ is absent. In case the distal nitrogen atom is part of an imine moiety, wherein a double bond is located between the distal nitrogen atom and the adjacent backbone atom of the linker, the compound of the invention may be represented by structure (Ic).

(Ic)

When the distal nitrogen atom is part of an imine moiety is in structure (Ic), it may either be cationic or neutral. The same options for N* as defined by structures (IIa) and (IIb), wherein $R^3$ is absent, apply. In case the distal nitrogen atom is neutral and part of an imine moiety, wherein a double bond is located between the distal nitrogen atom and the adjacent backbone atom of the linker, the compound according to the invention may also be referred to by general structure (Id). In case the distal nitrogen atom is cationic and part of an imine moiety, wherein a double bond is located between the distal nitrogen atom and the adjacent backbone atom of the linker, the compound according to the invention may also be referred to by general structure (Ie).

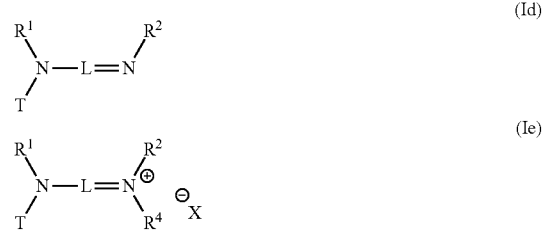

In the context of the present invention, the distal nitrogen being part of an imine moiety includes instances wherein the distal nitrogen atom is part of an heteroaromatic ring, in particular a pyrrole ring, a pyridine ring or a imidazole ring, in which instances a double bond is formally present between the distal nitrogen atom and the adjacent carbon atom either in the linker or in $R^2$. Preferred moieties comprising an imine moiety include guanidine, amidine and pyridine. For guanidine and amidine, one of the nitrogen atoms is substituted to form the connection with the amide nitrogen atom via linker L. For pyridine, one of the carbon atoms is substituted. When the distal nitrogen atom is part of an amine moiety, it is connected to the linker and $R^2$ via two single bonds, and $R^3$ is present. It is preferred that the distal nitrogen atom is part of an amine moiety, i.e. having three or four single bonds to each of $R^1$, $R^2$, $R^3$ and optionally $R^4$.

In the instance that $R^3$ is present, $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl groups or (halo)alkoxy moieties, preferably $R^3$ is H, $C_1$-$C_6$ alkyl, more preferably $R^3$ is H or $C_1$-$C_4$ alkyl, even more preferably $R^3$ is H or $C_1$-$C_2$ alkyl, wherein the alkyl moiety may be substituted with one or more halogen atoms, hydroxyl groups or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Preferred substituents for the alkyl moieties are halogen atoms and alkoxy moieties. Suitable moieties for $R^3$ include, preferably are limited to, H, methyl (Me), trifluoromethyl (—$CF_3$), ethyl (Et), isopropyl (iPr), cyclopropyl (-cPr), methylene cyclopropyl (—$CH_2cPr$), n-propyl (n-Pr), 2,2,2-trifluoroethyl (—$CH_2CF_3$), 2-hydroxy-ethyl (—$CH_2CH_2OH$), and methoxymethyl (—$CH_2OCH_3$), more preferably $R^3$ is H or methyl (Me), most preferably $R^3$ is H. Alternatively, $R^3$ is preferably $C_1$-$C_4$ alkyl, wherein the alkyl moiety may be substituted with one or more halogen atoms or (halo)alkoxy moieties, more preferably $R^3$ is $C_1$-$C_2$ alkyl, wherein the alkyl moiety may be substituted with one or more halogen atoms or (halo)alkoxy moieties.

In case the distal nitrogen atom is in cationic form, it formally originates from protonation or alkylation, preferably protonation or methylation of a trivalent nitrogen atom. The trivalent nitrogen atom is preferably an amine moiety, either primary, secondary or tertiary, or an imine moiety, either primary or secondary. The counter ion (X) of the cationic distal nitrogen atom is a negatively charged ion, preferably a monovalent negatively charged ion, more preferably an anion as indicated herein below. The synthesis of the compounds of the invention does not need to encompass the protonation or alkylation of an amine or imine nitrogen atom. The cationic distal nitrogen atom may also be formed via a different route. As such, the cationic distal nitrogen atom only "formally" originates from the protonation or alkylation of an amine or imine nitrogen atom.

$R^4$ is the substituent on the cationic distal nitrogen atom, which originates from formal protonation or alkylation of the amine or imine moiety. Thus, the compound according to this embodiment, in view of the presence of the cationic nitrogen atom and X, is a salt, preferably a pharmaceutically acceptable salt. Pharmaceutically acceptable salts are those salts that are suitable to be administered as drugs or pharmaceuticals to humans and/or animals. The pharmaceutically acceptable salts of the amine or imine moiety of the compound according to the invention are known to those skilled in the art, and originate from formal treatment of the compound with an acid (protonation agent) or an alkylating agent. Suitable acids include organic acids or inorganic acids. Examples of inorganic acids include, but are not limited to, hydrochloric acid (HCl), hydrobromic acid (HBr), hydroiodic acid (HI), sulphuric acid ($H_2SO_4$), nitric acid ($HNO_3$), trifluoroacetic acid (TFAH or $CF_3CO_2H$) and phosphoric acid ($H_3PO_4$). Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids and salicylic acid. When an acid as exemplified here is used to formally prepare the salt, $R^4$ is hydrogen, and the type of acid determines counter ion X. Alternatively, the salt can be formed by formal treatment with an alkylating agent. Suitable alkylating agents include, but are not limited to, $C_1$-$C_6$ alkyl halides (such as methyl iodide, ethyl iodide, propyl iodide, butyl chloride, butyl fluoride, butyl bromide), dimethyl sulphate, dimethyl carbonate, methyl triflate, methyl fluorosulfonate, methyl chlorosulfonate, methyl methanesulfonate and methyl benzenesulfonate. The salt may be prepared by actual treatment of the non-salt compound with an acid or alkylation agent, as indicated above, or via other means known in the art and/or exemplified further below.

$R^4$ is selected from hydrogen (H) or $C_1$-$C_6$ alkyl, wherein the alkyl moiety may be substituted with one or more halogen atoms or (halo)alkoxy moieties, preferably $R^4$ is H or $C_1$-$C_4$ alkyl, wherein the alkyl moiety may be substituted with one or more halogen atoms or (halo)alkoxy moieties, more preferably $R^4$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^4$ include, preferably are limited to, H, methyl (Me), trifluoromethyl (—$CF_3$), ethyl (Et), isopropyl (iPr), cyclopropyl (-cPr), methylene cyclopropyl (—$CH_2cPr$), n-propyl (n-Pr), 2,2,2-trifluoroethyl (—$CH_2CF_3$), methoxymethyl (—$CH_2OCH_3$). Even more preferably $R^4$ is H or methyl (Me), most preferably $R^4$ is H.

X can be any anion, preferably a physiologically or pharmaceutically acceptable anion, more preferably a monovalent anion. X is preferably selected from F, Cl, Br, I, $HSO_4$, $NO_3$, TFA ($CF_3CO_2$), formate, acetate, propionate, glycolate, pyruvate, oxalate, maleate, malonate, succinate, fumarate, tartarate, citrate, benzoate, cinnamate, mandelate, sulfonate and salicylate. Preferably, X is Cl, I, TFA or formate, more preferably Cl, I, TFA or formate, even more preferably X is Cl or formate, most preferably X is Cl. When the cationic nitrogen atom originates from formal protonation, this protonation is preferably accomplished with hydrogen chloride (HCl), trifluoroacetic acid (TFAH or $CF_3CO_2H$) or formic acid (HCOOH), more preferably with HCl or formic acid. Formal methylation is preferably accomplished with methyl iodide (MeI). Thus, in a preferred embodiment, $R^4$=Me when X=I$^-$, and $R^4$=H when X=Cl$^-$, TFA$^-$ or formate.

Appropriate linkers L to connect the amide nitrogen atom to the distal nitrogen atom are linkers preferably comprising 1 to 10 optionally substituted backbone atoms more preferably comprising 1 to 8 optionally substituted backbone atoms. L may thus comprise 1, 2, 3, 4, 5, 6, 7, 8, 9 or 10 optionally substituted backbone atoms. It is preferred that linker L comprises 1 to 10 optionally substituted backbone atoms selected from carbon, nitrogen and oxygen. Herein, backbone atoms are those atoms that make up the shortest chain between the amide nitrogen atom and the distal nitrogen atom. The backbone may be a linear structure, but (part of) the backbone may also be part of a cyclic structure. When the backbone is part a cyclic structure, the backbone is defined as the shortest chain between the amide nitrogen atom and the distal nitrogen atom. In one embodiment, one of the backbone atoms comprises a substituent $R^5$, and one of the backbone atoms comprises a substituent $R^{5'}$, preferably two different backbone atoms comprise the substituents $R^5$ and $R^{5'}$, wherein $R^5$ and $R^{5'}$ are joined to form a cyclic structure, preferably a 4-10-membered cyclic structure, more preferably a 5-8-membered cyclic structure, most preferably a 6-membered cyclic structure. In this embodiment, the amide nitrogen atom and the distal nitrogen atom are not included in the cyclic structure, but instead only part of the backbone of the linker is included. In a preferred embodiment, this connection between the backbone atom(s) of the linker, bearing the $R^5$ and $R^{5'}$ substituents, is a —$(CH_2)_n$— bridge, wherein n=1-6, preferably a —$CH_2$—$CH_2$— or —$CH_2$—$CH_2$—$CH_2$— bridge, wherein one to six, preferably two or three, carbon atoms are present between the substituted backbone atom(s) of the linker.

In a preferred embodiment, the backbone atoms are selected from carbon, nitrogen and oxygen, preferably from carbon and nitrogen. Such a backbone according to this preferred embodiment may be identified as $C_{n-m}N_m$, wherein n designates the total number of atoms in the backbone, and m the number of nitrogen atoms in the backbone. Each of n and m is a non-negative integer. Suitable linkers have n=1-10 and m=0-4, preferably n=2-7 and m=0-3, more preferably n=4-7 and m=0-2. Especially preferred linkers have a backbone identified as $C_{n-m}N_m$, wherein n=2 and m=0 ($C_2$); n=5 and m=1 ($C_4N$); n=3 and m=0 ($C_3$); n=4 and m=1 ($C_3N$); n=7 and m=2 ($C_5N_2$); n=4 and m=0 ($C_4$); n=6 and m=1 ($C_5N$); or n=5 and m=0 ($C_5$). Most preferably, all backbone atoms are carbon atoms (m=0).

To fulfil their valence requirements, the carbon and nitrogen backbone atoms of the linker may bear hydrogen atoms, may be substituted, or double or triple bonds may be present between adjacent backbone atoms, as will be understood by the skilled person. In the context of the invention, hydrogen is not regarded a substituent. Whenever an oxygen atom is present as backbone atom in the linker, the skilled person will understand that the oxygen backbone atom bears no hydrogen atoms, substituents or double or triple bonds. Triple bonds may be present between two carbon atoms of the backbone. The backbone atoms, together with the hydrogen atoms and/or the substituents, constitute the linker. In the context of the present invention, "optionally substituted" is used to indicate that an (backbone) atom may bear one or more substituents, or may bear no substituents and sufficient hydrogen atoms may be present instead, to fulfil the valence requirements of said (backbone) atom.

Suitable substituents include but are not limited to halogen, $NH_2$, $NHR^6$, $N(R^6)_2$, $NHNH_2$, $N_3$, $NHC(=O)R^6$, $NHC(=O)NHR^6$, $NHC(=O)NH_2$, $NHC(=O)OR^6$, OH, $OR^6$, $OC(=O)R^6$, $R^6$ (e.g. alkyl, cycloalkyl), aralkyl, alkenyl, alkynyl, aryl, heteroaryl, $OC(=O)OR^6$, $OC(=O)NHR^6$, $O(SO_2)R^6$, $O(SO_2)OH$, $O(PO_2)OH$, SH, $SR^6$, $C(=O)R^6$, alkyl-$NH_2$, alkyl-OH, alkyl-SH, $C(=O)CF_3$, $C(=O)OR^6$, $C(=O)OH$, $C(=O)H$, $C(=O)OR^6$, $C(=O)NH_2$, $C(=O)NMe_2$, $C(=O)N(R^6)_2$, $C(=S)NH_2C(=S)SH$, CN, NC, CNO, ONC, OCN, SCN, SNC, CNS, $S(=O)R^6$, $S(=O)_2R^6$, $S(=O)_2(OH)$, $P(=O)(OH)_2$ or $P(=O)(OH)(OR^6)$. Atoms having two or more remaining valencies, such as carbon backbone atoms, may bear a double bonded substituent, such as oxo (=O), imino (=NH or =$NR^6$), thioxo (=S), alkylidene (=$CH_2$ or =$CHR^6$ or =$C(R^6)_2$). Herein, each $R^6$ is independently an alkyl moiety, preferably a $C_1$-$C_6$ alkyl moiety, more preferably a $C_1$-$C_2$ alkyl moiety. Within $R^6$, one or more $CH_2$ moieties may each independently be replaced by one of O, S or NH, and/or one or more CH moieties may be replaced by N. In addition, two substituents on the same atom or on different atoms may be joined to form cyclic structures. If two substituents on a single backbone atom are joined in a cyclic structure, this cyclic structure may be regarded as being connected via a spiro junction to the backbone. If two substituents on different backbone atoms are joined in a cyclic structure, part of this cyclic structure is (part of) the backbone, and the backbone is considered to be the shortest chain of atoms between the amide nitrogen atom and the distal nitrogen atom. The cyclic structures formed as such may be all-carbon or may comprise 0-3 heteroatoms (e.g. N, O, S and/or P), and may comprise 0-3 double bonds. All atoms in these cyclic structures may optionally be substituted. Examples of suitable cyclic structures are optionally substituted cycloalkyl, optionally substituted cycloheteroalkyl, optionally substituted aryl or optionally substituted heteroaryl. As further indicated below, a cyclic structure may also be formed by joining one substituent on a backbone atom with $R^1$ on the amide nitrogen atom or with $R^2$ on the distal nitrogen atom.

In the context of the present invention, the term "alkyl" refers to saturated aliphatic groups including straight-chain, branched-chain, cyclic groups, and combinations thereof, having the number of carbon atoms specified, or if no number is specified, preferably having up to 12 carbon atoms. "Straight-chain alkyl" or "linear alkyl" group refers to alkyl groups that are neither cyclic nor branched, commonly designated as "n-alkyl" groups. One subset of alkyl groups is $C_1$-$C_6$ alkyl, which includes groups such as methyl, ethyl, n-propyl, isopropyl, butyl, n-butyl, isobutyl, sec-butyl, t-butyl, pentyl, n-pentyl, hexyl, cyclopropyl, cyclobutyl, cyclopentyl, cyclohexyl, and any other alkyl group containing between one and six carbon atoms, where the $C_1$-$C_6$ alkyl groups can be attached via any valence on the $C_1$-$C_6$ alkyl groups.

In one embodiment, the backbone atoms are optionally substituted with one or more substituents selected from the group consisting of $R^6$, carboxy, oxo, and primary amino or a backbone atom may be joined with $R^1$ to form a 4-10-membered cyclic structure and/or a backbone atom may be joined with $R^2$ to form a 4-10-membered cyclic structure, or two backbone atoms may be joined to form a cyclic structure, wherein $R^6$ is as defined above, preferably $R^6$ is $C_1$-$C_6$ alkyl, more preferably $C_1$-$C_2$ alkyl. Preferred substituents of the backbone atoms are alkyl, such as methyl (Me or —$CH_3$), carboxyl (—$C(=O)OH$), oxo (=O) and primary amino (—$NH_2$).

Preferred linkers L are identified here below as $L^1$ to $L^{28}$. More preferred are $L^1$ to $L^{26}$:

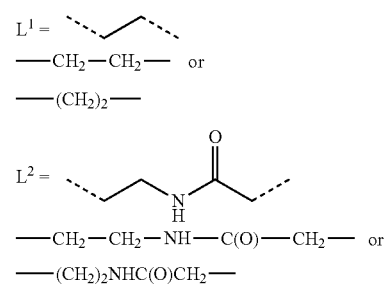

$L^1 =$
—$CH_2$—$CH_2$— or
—$(CH_2)_2$—

$L^2 =$
—$CH_2$—$CH_2$—NH—C(O)—$CH_2$— or
—$(CH_2)_2NHC(O)CH_2$—

-continued $L^3 =$ 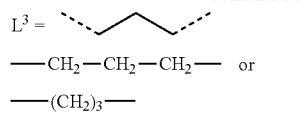

—CH$_2$—CH$_2$—CH$_2$— or

—(CH$_2$)$_3$—

$L^4 =$ 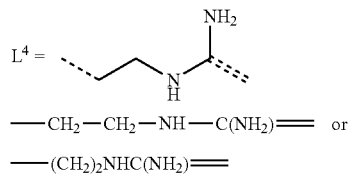

—CH$_2$—CH$_2$—NH—C(NH$_2$)= or

—(CH$_2$)$_2$NHC(NH$_2$)=

$L^5 =$ 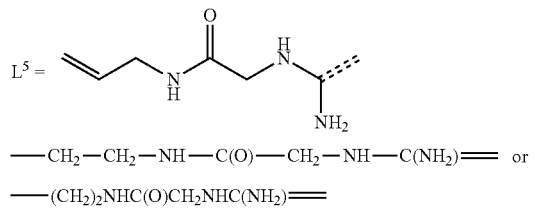

—CH$_2$—CH$_2$—NH—C(O)—CH$_2$—NH—C(NH$_2$)= or

—(CH$_2$)$_2$NHC(O)CH$_2$NHC(NH$_2$)=

$L^6 =$ 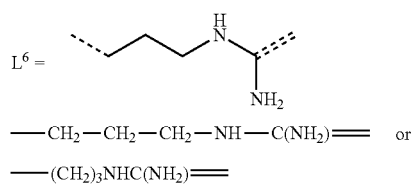

—CH$_2$—CH$_2$—CH$_2$—NH—C(NH$_2$)= or

—(CH$_2$)$_3$NHC(NH$_2$)=

$L^7 =$ 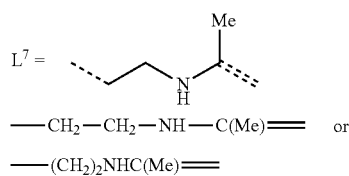

—CH$_2$—CH$_2$—NH—C(Me)= or

—(CH$_2$)$_2$NHC(Me)=

$L^8 =$ 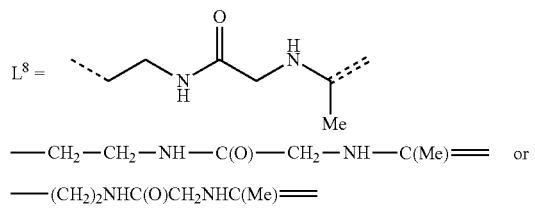

—CH$_2$—CH$_2$—NH—C(O)—CH$_2$—NH—C(Me)= or

—(CH$_2$)$_2$NHC(O)CH$_2$NHC(Me)=

$L^9 =$ 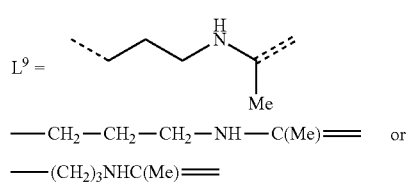

—CH$_2$—CH$_2$—CH$_2$—NH—C(Me)= or

—(CH$_2$)$_3$NHC(Me)=

$L^{10} =$ 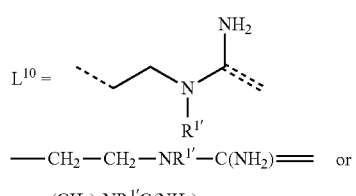

—CH$_2$—CH$_2$—NR$^{1'}$—C(NH$_2$)= or

—(CH$_2$)$_2$NR$^{1'}$C(NH$_2$)=

$L^{11} =$ 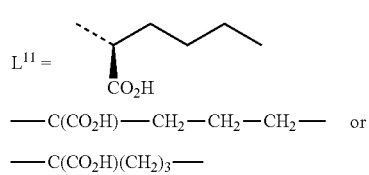

—C(CO$_2$H)—CH$_2$—CH$_2$—CH$_2$— or

—C(CO$_2$H)(CH$_2$)$_3$—

$L^{12} =$ 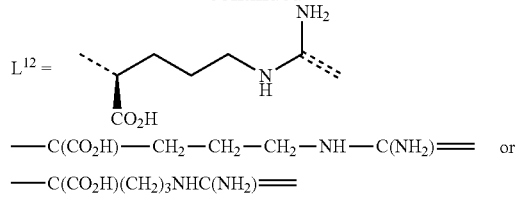

—C(CO$_2$H)—CH$_2$—CH$_2$—CH$_2$—NH—C(NH$_2$)= or

—C(CO$_2$H)(CH$_2$)$_3$NHC(NH$_2$)=

$L^{13} =$ 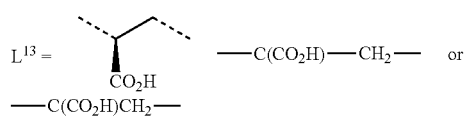 —C(CO$_2$H)—CH$_2$— or

—C(CO$_2$H)CH$_2$—

$L^{14} =$ 

—C(CO$_2$H)—CH$_2$—CH$_2$— or —C(CO$_2$H)(CH$_2$)$_2$—

$L^{15} =$ 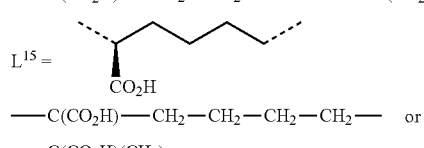

—C(CO$_2$H)—CH$_2$—CH$_2$—CH$_2$—CH$_2$— or

—C(CO$_2$H)(CH$_2$)$_4$—

$L^{16} =$ 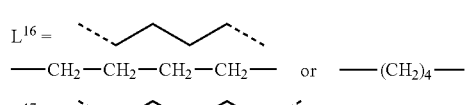

—CH$_2$—CH$_2$—CH$_2$—CH$_2$— or —(CH$_2$)$_4$—

$L^{17} =$ 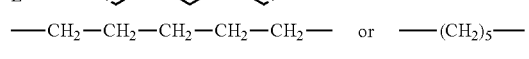

—CH$_2$—CH$_2$—CH$_2$—CH$_2$—CH$_2$— or —(CH$_2$)$_5$—

$L^{18} =$ 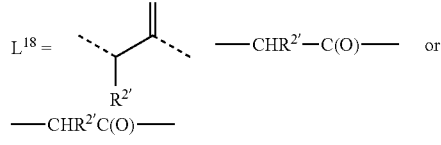 —CHR$^{2'}$—C(O)— or

—CHR$^{2'}$C(O)—

$L^{19} =$ 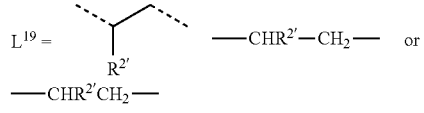 —CHR$^{2'}$—CH$_2$— or

—CHR$^{2'}$CH$_2$—

$L^{20} =$ 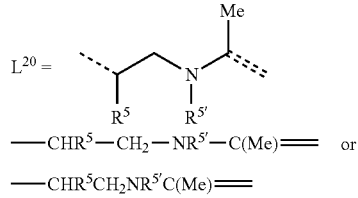

—CHR$^5$—CH$_2$—NR$^{5'}$—C(Me)= or

—CHR$^5$CH$_2$NR$^{5'}$C(Me)=

$L^{21} =$ 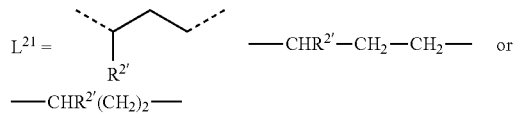 —CHR$^{2'}$—CH$_2$—CH$_2$— or

—CHR$^{2'}$(CH$_2$)$_2$—

$L^{22} =$ 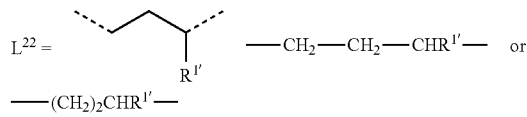 —CH$_2$—CH$_2$—CHR$^{1'}$— or

—(CH$_2$)$_2$CHR$^{1'}$—

$L^{23} =$ 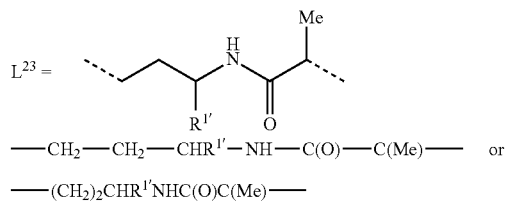

—CH$_2$—CH$_2$—CHR$^{1'}$—NH—C(O)—C(Me)— or

—(CH$_2$)$_2$CHR$^{1'}$NHC(O)C(Me)—

-continued

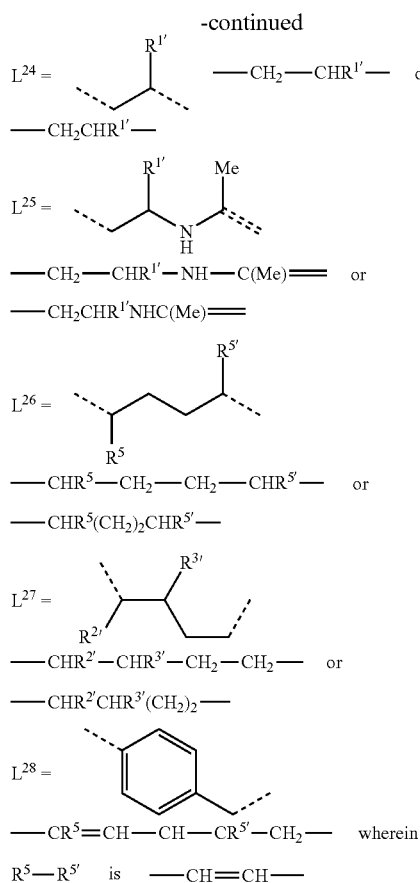

—CH$_2$CHR$^{1'}$—

L$^{25}$ =

—CH$_2$—CHR$^{1'}$—NH—C(Me)═  or

—CH$_2$CHR$^{1'}$NHC(Me)═

L$^{26}$ =

—CHR$^5$—CH$_2$—CH$_2$—CHR$^{5'}$—  or

—CHR$^5$(CH$_2$)$_2$CHR$^{5'}$—

L$^{27}$ =

—CHR$^{2'}$—CHR$^{3'}$—CH$_2$—CH$_2$—  or

—CHR$^{2'}$CHR$^{3'}$(CH$_2$)$_2$—

L$^{28}$ =

—CR$^5$═CH—CH—CR$^{5'}$—CH$_2$—  wherein

R$^5$—R$^{5'}$  is  —CH═CH—

Herein, it is preferred that the dashed bond at the left side of each of the structures for L$^1$ to L$^{28}$ indicates the bond between the linker and the amide nitrogen atom, and the dashed bond at the right side of each of the structures for L$^1$ to L$^{28}$ indicates the bond between the linker and the distal nitrogen atom.

Each occurrence of R$^{1'}$ represents the connection of a second linker between the linker and the amide nitrogen atom, wherein R$^{1'}$ is joined with R$^1$ via the second linker, thus forming a 4-10-membered cyclic structure, preferably a 5-8-membered cyclic structure, most preferably a 6-membered cyclic structure, which is built up from the amide nitrogen atom, 1-4 atoms of the backbone of the linker, and 1-4 atoms which make up the bridge joining R$^1$ and R$^{1'}$. Likewise, each occurrence of R$^{2'}$ represents the connection of a second linker between the linker and the cationic nitrogen atom, wherein R$^{2'}$ is joined with R$^2$ via the second linker, thus forming a 4-10-membered cyclic structure, preferably a 5-8-membered cyclic structure, most preferably a 6-membered cyclic structure, which is built up from the cationic nitrogen atom, 1-4 atoms of the backbone of the linker, and 1-4 atoms which make up the bridge joining R$^2$ and R$^{2'}$. Likewise, each occurrence of R$^5$ and R$^{5'}$ represent the connection of a second linker between one backbone atom of the linker, bearing R$^5$, and another backbone atom of the linker, bearing R$^{5'}$, wherein R$^{5'}$ is joined with R$^5$ via the second linker, thus forming a 4-10-membered cyclic structure, preferably a 5-8-membered cyclic structure, most preferably a 6-membered cyclic structure, which is built up from 2-5 atoms of the backbone of the linker, and 1-5 atoms which make up the bridge joining R$^5$ and R$^{5'}$. Thus, in linkers L$^{10}$, L$^{22}$, L$^{23}$, L$^{24}$ and L$^{25}$, R$^{1'}$ is joined to R$^1$ via a second linker, preferably a —CH$_2$—CH$_2$— or —CH$_2$—CH$_2$—CH$_2$— bridge, more preferably a —CH$_2$—CH$_2$— bridge. Thus, in a compound comprising linker L$^{10}$, wherein R$^{1'}$ and R$^1$ are joined via a —CH$_2$—CH$_2$— bridge, the amide nitrogen atom is embedded in a six-membered cyclic structure, which is built up from the amide nitrogen atom, two carbon atoms and one nitrogen atom of the backbone of the linker, and two more carbon atoms which make up the bridge of R$^1$ and R$^{1'}$. This —CH$_2$—CH$_2$— bridge between the amide nitrogen atom and the central nitrogen atom in the backbone of linker L$^{10}$ may be represented as L$^1$. Likewise, in linkers L$^{18}$, L$^{19}$ and L$^{21}$, R$^{2'}$ is joined to R$^2$ via a second linker, preferably a —CH$_2$—CH$_2$— or —CH$_2$—CH$_2$—CH$_2$— bridge, more preferably a CH$_2$—CH$_2$—CH$_2$— bridge. Likewise, in linker L$^{20}$ and L$^{26}$, R$^{5'}$ is joined to R$^5$ via a second linker, preferably a —CH$_2$—CH$_2$— or —CH$_2$—CH$_2$—CH$_2$— bridge, more preferably a —CH$_2$—CH$_2$— bridge.

Linker L$^{26}$ comprises a disubstituted cycloalkyl moiety, preferably a disubstituted cyclohexyl moiety, and may thus occur in either the cis-form or the trans-form, preferably in the trans-form.

Linker L$^{27}$ comprises a bicyclic cycloalkyl moiety, preferably a bicyclic cyclooctyl moiety. When L=L$^{27}$ it is highly preferred that L, R$^2$, and R$^3$ together comprise 7, 8, 9, 10, 11, or 12 carbon atoms. Most preferably L27 is comprised in an azabicyclooctane such as azabicyclo[2.2.2]octane.

Linkers L$^{11}$, L$^{12}$, L$^{13}$, L$^{14}$, L$^{16}$, L$^{18}$ (as long as R$^2$—R$^{2'}$ is not —C(O)—), L$^{19}$ (as long as R$^2$—R$^{2'}$ is not —CH$_2$—), L$^{20}$ (as long as R$^5$—R$^{5'}$ is not —CH$_2$—), L$^{21}$ (as long as R$^2$—R$^{2'}$ is not —CH$_2$—CH$_2$—), L$^{22}$ (as long as R$^1$—R$^{1'}$ is not —CH$_2$—CH$_2$—), L$^{23}$ (as long as R$^1$—R$^{1'}$ is not —CH$_2$—CH$_2$—), L$^{24}$ (as long as R$^1$—R$^{1'}$ is not —CH$_2$—) and L$^{25}$ (as long as R$^1$—R$^{1'}$ is not —CH$_2$—) comprise an additional stereocenter. The stereoisomer, when indicated in the structures of those linkers, above is meant as illustrative, not as limiting. As indicated further above, each stereocenter present in the compounds according to the invention may individually be present in each of its stereoisomeric forms, either S or R, or as a mixture of both isomers in any ratio. In view of the stereocenter already present at the 2-position of T, the compounds having these linkers may be (R,R); (S,R); (R,S); or (S,S). Throughout the description, the first designator (R or S) of the configuration is for the 2-position of T, and the second designator thereof defines the configuration of the additional stereocenter that may be present in the compound according to the invention. For L$^{23}$ the methyl group as indicated by "Me" in the table above is preferably (S).

In preferred embodiments linkers are Especially preferred linkers are L$^5$, L$^8$, L$^{11}$, L$^{12}$, L$^{16}$, L$^{17}$, L$^{19}$, L$^{21}$, L$^{26}$, L$^{27}$, and L$^{28}$. Especially preferred linkers are L$^5$, L$^8$, L$^{11}$, L$^{12}$, L$^{16}$, L$^{17}$, L$^{19}$, L$^{21}$ and L$^{26}$. Even more preferred linkers are L$^{11}$, L$^{16}$, L$^{19}$ and L$^{26}$, and most preferably the linker is L$^{19}$. Preferably, L$^{19}$ is combined with R$^2$—R$^{2'}$=L$^1$ or L$^3$, most preferably with R$^2$—R$^{2'}$=L$^3$. Preferably, L$^{21}$ is combined with R$^2$—R$^{2'}$=L$^1$ or L$^3$, most preferably with R$^2$—R$^{2'}$=L$^1$. Preferably, L$^{26}$ is combined with R$^5$—R$^{5'}$=L$^1$ or L$^3$, more preferably with R$^5$—R$^{5'}$=L$^1$, most preferably wherein the cyclohexyl is trans-1,4-disubstituted. Especially preferred is the combination of linker L$^{19}$ with R$^2$—R$^{2'}$=L$^3$ and R$^3$=H, Me, Et, iPr, CH$_2$OCH$_3$ or CH$_2$CF$_3$, more preferably R$^3$=Me, Et, iPr or CH$_2$CF$_3$, most preferably R$^3$=H In case N* is according to structure (IIa), it is preferred that linker L contains 1-5 optionally substituted backbone atoms and/or linker L contains at least one backbone atom other than carbon. In case N* is according to structure (IIa), it is especially preferred that the distal nitrogen atom is connected to a backbone atom of the linker via a second linker wherein $R^2$ is joined with $R^{2'}$, more preferably wherein the cyclic structure thus formed is a piperidine ring, a pyrrolidine ring, an imidazolidine ring, a pyrazolidine ring or an azepane ring, most preferably a piperidine ring, and/or at least one of the backbone atoms is substituted with a carboxylic acid moiety. In case N* is according to structure (IIa), it is preferred that L is any one of $L^2$, $L^4$-$L^{21}$, $L^{23}$, $L^{25}$, $L^{26}$, $L^{27}$, and $L^{28}$ especially preferred that L is any one of $L^2$, $L^4$-$L^{21}$, $L^{23}$, $L^{25}$ and $L^{26}$, more preferably one of $L^5$, $L^8$, $L^{11}$, $L^{12}$, $L^{16}$, $L^{17}$, $L^{19}$, $L^{21}$ and $L^{26}$. In case N* is according to structure (IIb), it is preferred that $R^4$ is H or Me, more preferably $R^4$ is H, and X is Cl, I, TFA or formate, even more preferably X is Cl or formate, most preferably X is Cl. In case N* is according to structure (IIb), it is preferred that linker L contains 3-10 backbone atoms, or 2 backbone atoms of which one is connected to the distal nitrogen atom via a second linker. In case N* is according to structure (IIb), it is preferred that L is any one of $L^2$-$L^{28}$, especially preferred that L is any one of $L^2$-$L^{26}$, more preferably one of $L^5$, $L^8$, $L^{11}$, $L^{12}$, $L^{16}$, $L^{17}$, $L^{19}$, $L^{21}$ and $L^{26}$.

In one embodiment, linker L is $L^1$ and $R^1$ and $R^2$ are joined together in a cyclic structure via a second linker $L^1$, thus forming a six-membered piperazine ring including in total four carbon atoms from the two linkers, the amide nitrogen atom and the distal nitrogen atom. In one embodiment, linker L is $L^{19}$ and $R^2$ and $R^{2'}$ are joined together in a cyclic structure via a second linker $L^3$, thus forming a six-membered piperidine ring including in total five carbon atoms from the linkers and the distal nitrogen atom.

In a preferred embodiment, the compound is represented by general structure (I), wherein:
L is a linker between the amide nitrogen atom and the distal nitrogen atom;
N* is according to structure (IIa);
T is according to structure (IIIa) or (IIIb), wherein $R^7$ is a $C_1$-$C_6$ alkyl moiety;
$R^1$ is selected from hydrogen (H), $C_1$-$C_6$ alkyl or $C_1$-$C_6$ alkenyl, or $R^1$ is joined with a backbone atom of the linker L in a cyclic structure;
$R^2$ is joined with a backbone atom of the linker L to form a cyclic structure selected from a piperidine ring, a pyrrolidine ring, an imidazolidine ring, a pyrazolidine ring or an azepane ring; and
$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety.

In an alternative preferred embodiment, the compound according to the invention is represented by general structure (I), wherein
L is a linker between the amide nitrogen atom and the distal nitrogen atom comprising 3-10 backbone atoms, or 2 backbone atoms of which one is connected to the distal nitrogen atom via a second linker;
N* is according to structure (IIb);
T is according to structure (IIIa) or (IIIb), wherein $R^7$ is a $C_1$-$C_6$ alkyl moiety;
$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety;
$R^4$ is selected from hydrogen (H) or $C_1$-$C_6$ alkyl, wherein the alkyl moiety may be substituted with one or more halogen atoms or (halo)alkoxy moieties; and
X is an anion, preferably a pharmaceutically acceptable anion.

Particularly preferred compounds in the context of the present invention are identified here below by structures (VI)-(IX). Thus, in a preferred embodiment, the compound of general structure (I) is represented by structure (VI):

Herein, $R^2$ is joined with a backbone atom via a second linker forming a cyclic structure, thus N* is —$NR^3$ or —$N^+R^3R^4X^-$. Herein, $R^3$, $R^4$, X and T are as defined above. Preferably, T is according to structure (IIIa) or (IIIb), more preferably according to structure (IVa) or (IVb), most preferably according to structure (IIIb) or (IVb). In the compound according to structure (VI), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VI) may be (R,R); (S,R); (R,S); or (S,S), preferably it is (S,R).

In a preferred embodiment, the compound of general structure (I) is represented by structure (VIIa) or (VIIb):

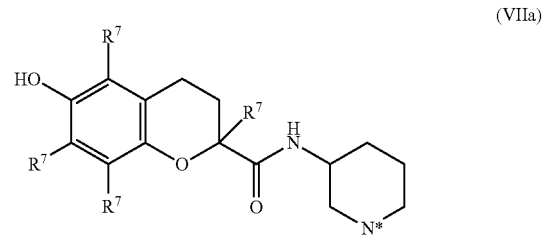

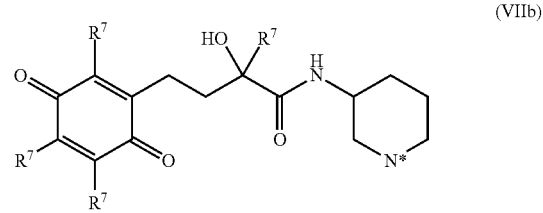

Herein, $R^2$ is joined with a backbone atom via a second linker forming a cyclic structure, thus N* is —$NR^3$ or —$N^+R^3R^4X^-$. Herein, $R^3$, $R^4$, X and $R^7$ are as defined above. In the compound according to structure (VIIa) or (VIIb), $R^7$ is preferably methyl. In the compound according to structure (VIIa) or (VIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIa) or (VIIb) may be (R,R); (S,R); (R,S); or (S,S), preferably it is (S,R). In one embodiment, the compound of general structure (I) is represented by structure (VIIa). In an alternative embodiment, the compound of general structure (I) is represented by structure (VIIb). In highly preferred embodiments, the invention provides a compound for use as described above, wherein the compound is represented by structure (VIIb), wherein each $R^7$ is methyl; N* is —$NR^3$ or —$N^+R^3R^4X^-$; X is as defined above and is preferably $Cl^-$; $R^3$ is as defined above and is preferably hydrogen; and $R^4$ is as defined above and is preferably hydrogen. It is even more preferred for this compound to be of the S,R configuration.

In a preferred embodiment, the compound of general structure (I) is represented by structure (VIIIa) or (VIIIb):

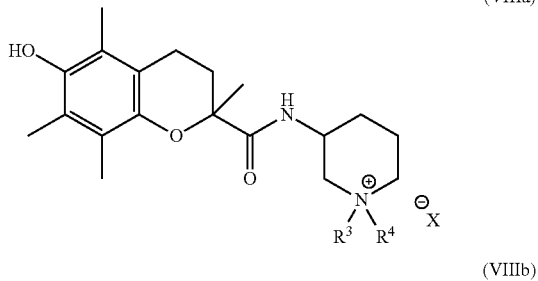

(VIIIa)

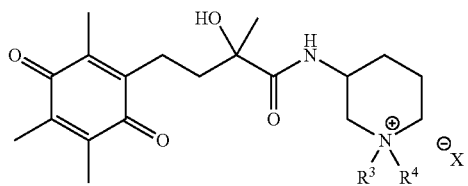

(VIIIb)

Herein, $R^2$ is joined with a backbone atom via a second linker forming a cyclic structure and N* is —$N^+R^3R^4X^-$. Herein, $R^3$, $R^4$ and X are as defined above. In the compound according to structure (VIIIa) or (VIIIb), $R^3$ is preferably H or $C_1$-$C_2$ alkyl, most preferably $R^3$ is H. In the compound according to structure (VIIIa) or (VIIIb), $R^4$ is preferably H or $C_1$-$C_2$ alkyl, most preferably $R^4$ is H. In the compound according to structure (VIIIa) or (VIIIb), X is preferably Cl, I, TFA or formate, most preferably X is $C_1$. In the compound according to structure (VIIIa) or (VIIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIIa) or (VIIIb) may be (R,R); (S,R); (R,S); or (S,S), preferably it is (S,R). In one embodiment, the compound of general structure (I) is represented by structure (VIIIa). In an alternative embodiment, the compound of general structure (I) is represented by structure (VIIIb).

In a preferred embodiment, the compound of general structure (I) is represented by structure (IXa) or (IXb):

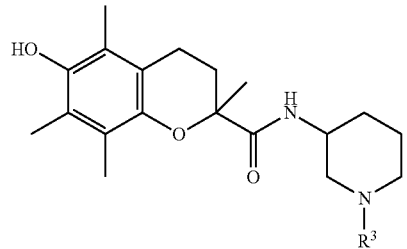

(IXa)

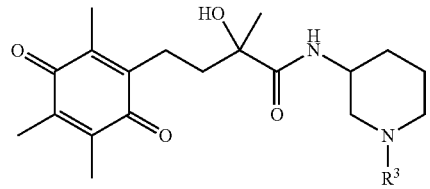

(IXb)

Herein, $R^2$ is joined with a backbone atom via a second linker forming a cyclic structure and N* is —$NR^3$. Herein, $R^3$ is as defined above. In the compound according to structure (VIIIa) or (VIIIb), $R^3$ is preferably H or $C_1$-$C_2$ alkyl, most preferably $R^3$ is H. In the compound according to structure (IXa) or (IXb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (IXa) or (IXb) may be (R,R); (S,R); (R,S); or (S,S), preferably it is (S,R). In one embodiment, the compound of general structure (I) is represented by structure (IXa). In an alternative embodiment, the compound of general structure (I) is represented by structure (IXb).

In a preferred embodiment, the compound is according to general structure (I), wherein T is represented by structure (IVa) or (IVb), N* is represented by structure (IIa) or by structure (IIb) wherein $R^4$=H and X=Cl, and wherein:

(A) L=$R^1R^2$=$L^1$, $R^3$=H;
(B) L=$R^1$=H, $R^2$=H, $R^3$=H;
(C) L=$L^2$, $R^1$=H, $R^2$=H, $R^3$=H;
(D) L=$L^3$, $R^1$=H, $R^2$=H, $R^3$=H;
(E) L=$L^4$, $R^1$=H, $R^2$=H, $R^3$=absent;
(F) L=$L^5$, $R^1$=H, $R^2$=H, $R^3$=absent;
(G) L=$L^6$, $R^1$=H, $R^2$=H, $R^3$=absent;
(H) L=$L^3$, $R^1$=H, $R^2$=Me, $R^3$=Me;
(I) L=$L^1$, $R^1$=H, $R^2$=Me, $R^3$=Me;
(J) L=$L^7$, $R^1$=H, $R^2$=H, $R^3$=absent;
(K) L=$L^8$, $R^1$=H, $R^2$=H, $R^3$=absent;
(L) L=$L^9$, $R^1$=H, $R^2$=H, $R^3$=absent;
(M) L=$L^{10}$, $R^1$—$R^{1'}$=$L^1$, $R^2$=H, $R^3$=absent;
(N) L=$L^{11}$, $R^1$=H, $R^2$=H, $R^3$=H;
(O) L=$L^{12}$, $R^1$=H, $R^2$=H, $R^3$=absent;
(P) L=$L^{13}$, $R^1$=H, $R^2$=H, $R^3$=H;
(Q) L=$L^{14}$, $R^1$=H, $R^2$=H, $R^3$=H;
(R) L=$L^{15}$, $R^1$=H, $R^2$=H, $R^3$=H;
(S) L=$L^{11}$, $R^1$=H, $R^2$=Me, $R^3$=Me;
(T) L=$L^{16}$, $R^1$=H, $R^2$=H, $R^3$=H;
(U) L=$L^{17}$, $R^1$=H, $R^2$=H, $R^3$=H;
(V) L=$L^{16}$, $R^1$=H, $R^2$=Me, $R^3$=Me;
(N) L=$L^{18}$, $R^1$=H, $R^2$—$R^{2'}$=$L^3$, $R^3$=H;
(X) L=$L^{19}$, $R^1$=H, $R^2$—$R^{2'}$=$L^3$, $R^3$=H;
(Y) L=$L^{20}$, $R^1$=H, $R^2$=H, $R^5$—$R^{5'}$=$L^3$, $R^3$=absent;
(Z) L=$L^{21}$, $R^1$=H, $R^2$—$R^{2'}$=$L^1$, $R^3$=H;

(AA) L=L$^{22}$, R$^1$—R$^{1'}$=L$^1$, R$^2$=H, R$^3$=H;
(AB) L=L$^{23}$, R$^1$—R$^{1'}$=L$^1$, R$^2$=H, R$^3$=H;
(AC) L=L$^{24}$, R$^1$—R$^{1'}$=L$^3$, R$^2$=H, R$^3$=H;
(AD) L=L$^{25}$, R$^1$—R$^{1'}$=L$^3$, R$^2$=H, R$^3$=absent;
(AE) L=L$^{26}$, R$^1$=H, R$^2$=H, R$^5$—R$^{5'}$=L$^1$, R$^3$=H.
(AF) L=L$^{19}$, R$^1$=H, R$^2$—R$^{2'}$=L$^3$, R$^3$=Me;
(AG) L=L$^{19}$, R$^1$=H, R$^2$—R$^{2'}$=L$^1$, R$^3$=H;
(AH) L=L$^{21}$, R$^1$=H, R$^2$—R$^{2'}$=L$^1$, R$^3$=Me;
(AI) L=L$^{27}$, R$^1$=H, R$^2$—R$^{2'}$=—CH$_2$—, R$^3$—R$^{3'}$=L$^1$, R$^4$=H, X=Cl;
(AJ) L=L$^{28}$, R$^1$=H, R$^2$=H, R$^3$=H, R$^4$=H, X=Cl.

It is thus preferred that the compound according to structure (I) is selected from compounds A-AJ defined above, more preferably from compounds A-AH defined above, even more preferably selected from compounds A-AJ based on general structure (IVb), most preferably selected from compounds A-AH based on general structure (IVb). Especially preferred compounds are selected from F, K, N, O, U, V, T, X, Z, AE, AF, AG, AH, AI, and AJ, more preferred compounds are selected from F, K, N, O, U, V, T, X, Z, AE, AF, AG and AH, even more preferably N, T, X and AE, most preferably X. Herein, N* is preferably represented by structure (IIb) wherein R$^4$=H and X=Cl, and the compound is preferably of general structure (IVb).

Compound F may have the R-configuration, the S-configuration or a mixture thereof, preferably compound F is a mixture of the R- and S-enantiomers, more preferably a racemic mixture. Compound K may have the R-configuration, the S-configuration or a mixture thereof, preferably compound K is a mixture of the R- and S-enantiomers, more preferably a racemic mixture. Compound N may have the R,R-configuration, R,S-configuration, S,R-configuration, the S,S-configuration or any mixture thereof, preferably compound N has the R,R-configuration or the S,R-configuration, most preferably the R,R-configuration. Compound O may have the R,R-configuration, R,S-configuration, S,R-configuration, the S,S-configuration or any mixture thereof, preferably compound O is a mixture of the R,S- and S,S-diastereomers more preferably about 1/1 (mol/mol) mixture. Compound U may have the R-configuration, the S-configuration or a mixture thereof, preferably compound U has the R-configuration or the S-configuration. Compound V may have the R-configuration, the S-configuration or a mixture thereof, preferably compound V has the R-configuration. Compound T may have the R-configuration, the S-configuration or a mixture thereof, preferably compound T has the R-configuration or the S-configuration, most preferably the R-configuration. Compound X may have the R,R-configuration, R,S-configuration, S,R-configuration, the S,S-configuration or any mixture thereof, preferably compound X has the R,S-configuration or the S,R-configuration, most preferably the S,R-configuration. Compound Z may have the R-configuration, the S-configuration or a mixture thereof, preferably compound Z is a mixture of the R- and S-enantiomers, more preferably a racemic mixture. Compound AE may have the R,trans-configuration, R,cis-configuration, S,trans-configuration, the S,cis-configuration or any mixture thereof, preferably compound AE has the R,trans-configuration or the S,trans-configuration, most preferably the R,trans-configuration. Compound AF may have the R,R-configuration, R,S-configuration, S,R-configuration, the S,S-configuration or any mixture thereof, preferably compound AF has the S,R-configuration. Compound AG may have the R,R-configuration, R,S-configuration, S,R-configuration, the S,S-configuration or any mixture thereof, preferably compound AG has the S,S-configuration or the S,R-configuration. Compound AH may have the R-configuration, the S-configuration or a mixture thereof, preferably compound AH has the S-configuration. Herein, the first designator (R or S) of the configuration is for the 2-position of T, and in case an additional stereocenter is present in the compound according to the invention, the second designator thereof defines the configuration thereof. Compound AJ may have the R,R-configuration, the R,S-configuration, the S,R-configuration, the S,S-configuration, or a mixture thereof, preferably compound AJ has the S,R-configuration or the R,R-configuration or a mixture thereof, most preferably compound AJ has the R,R-configuration.

Highly preferred compounds include compound N in the R,R-configuration (R,R—N), compound T in the R-configuration (R-T), compound AE in the R,trans-configuration (R,trans-AE), compound AJ in the R-configuration (R-AJ), and compound X in any configuration. The most preferred compounds include compound N in the R,R-configuration (R,R—N), compound T in the R-configuration (R-T), compound AE in the R,trans-configuration (R,trans-AE) and compound X in any configuration, most preferably the compound according to the invention is compound X in the S,R-configuration (S,R—X). In one embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein N* is represented by structure (IIb), wherein R$^4$=H and X=Cl, more preferably the compound according to the invention is compound X in the S,R-configuration (S,R—X), wherein N* is represented by structure (IIb), wherein R$^4$=H and X=Cl. In one embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein N* is represented by structure (IIa), most preferably the compound according to the invention is compound X in the S,R-configuration (S,R—X), wherein N* is represented by structure (IIa).

In one embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein the compound is of structure (IIIa), most preferably the compound according to the invention is compound X in the S,R-configuration (S,R—X), wherein the compound is of structure (IIIa).

In one embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein the compound is of structure (IIIa), wherein N* is represented by structure (IIb), wherein R$^4$=H and X=Cl, most preferably the compound according to the invention is compound X in the S,R-configuration (S,R—X), wherein the compound is of structure (IIIa) and wherein N* is represented by structure (IIb), wherein R$^4$=H and X=Cl.

In one embodiment, these most preferred compounds according to the invention are compound N in the R,R-configuration (R,R—N), compound T in the R-configuration (R-T), compound AE in the R,trans-configuration (R,trans- AE) and compound X in any configuration, and optionally compound AJ preferably as R,R-AJ, wherein the compound is of structure (IIIa), wherein N* is represented by structure (IIa), most preferably the compound according to the invention is compound X in the S,R-configuration (S,R—X), wherein the compound is of structure (IIIa) and wherein N* is represented by structure (IIa).

In one preferred embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein the compound is of structure (IIIb), most preferably the compound according to the invention is compound X in the S,R-configuration (S,R—X), wherein the compound is of structure (IIIb).

In one highly preferred embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein the compound is of structure (IIIb), wherein N* is represented by structure (IIb), wherein $R^4$=H and X=Cl, most preferably the compound according to the invention is compound X in the S,R-configuration (S,R—X), wherein the compound is of structure (IIb) and wherein N* is represented by structure (IIb), wherein $R^4$=H and X=Cl.

In another highly preferred embodiment, these most preferred compounds according to the invention are compound N in the R,R-configuration (R,R—N), compound T in the R-configuration (R-T), compound AE in the R,trans-configuration (R,trans-AE) and compound X in any configuration, and optionally compound AJ preferably as R,R-AJ, wherein the compound is of structure (IIIb), wherein N* is represented by structure (IIa), most preferably the compound according to the invention is compound X in the S,R-configuration (S,R—X), wherein the compound is of structure (IIIb) and wherein N* is represented by structure (IIa).

Compounds of the open configuration (comprising a chromanyl quinone framework, preferably of general structure (IIIb)) have been found to be more potent mPGES-1 inhibitors than compounds of the closed configuration (comprising a chromanyl framework, preferably of general structure (IIIa)). However, compounds of the closed configuration have shown a higher oral bioavailability than compounds of the open configuration.

The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

The compounds of the invention are selective mPGES-1 inhibitors and can be used as such. The term "selective mPGES-1 inhibitor" as used herein refers to a substance which is capable of inhibiting or suppressing the (enhanced) expression and/or functional activity of mPGES-1 in cells or in subjects but does not have any or significant inhibitory effect on the expression of cyclooxygenase in particular COX-2. The compounds of the invention are therefore capable of selectively reducing the level of $PGE_2$, without affecting the levels of other prostaglandins, such as e.g. PGD2, 6-keto $PGF_{1\alpha}$ and $PGI_2$. The inventors believe that since the selective mPGES-1 inhibitors of the invention have no significant or have no effect on the expression/activity of cyclooxygenases, the prostaglandin homeostasis in cells or subjects can be maintained in a relatively stable manner, thereby alleviating diseases or symptoms associated with the overexpression of mPGES-1 and at the same time with a reduced risk of suffering from adverse effects induced by COX-1/2 inhibition, such as cardiovascular events and gastric damage.

Therefore, the compounds of the invention can be used in methods for treating or preventing enhanced mPGES-1 expression or activity, and/or treating, preventing and/or suppressing symptoms associated with enhanced mPGES-1 expression or activity. Such enhanced or increased activity of mPGES-1 is usually the result of induced expression the mPGES-1 enzyme, i.e. overexpression of mPGES-1, and will produce increased levels of $PGE_2$. Enhanced mPGES-1 activity, overexpression of mPGES-1 and increased levels of $PGE_2$ are herein thus understood as higher than in corresponding normal, e.g. non-inflamed, conditions, subjects, organs, tissues or cells.

In the context of this invention, the activity of an enzyme preferably relates to the amount of reactions is catalyzes per time unit. In the context of this invention, the amount of expression of an enzyme preferably relates to the amount of enzyme molecules that are present at a given moment, or that are produced, preferably in a cell, per time unit.

Compounds of the invention are thus expected to be useful in the treatment of inflammation. The term "inflammation" will be understood by those skilled in the art to include any condition characterized by a localized or a systemic protective response, which may be elicited by physical trauma, infection, chronic diseases, such as those mentioned hereinafter, and/or chemical and/or physiological reactions to external stimuli (e.g. as part of an allergic response). Any such response, which may serve to destroy, dilute or sequester both the injurious agent and the injured tissue, may be manifested by symptoms mediated by enhanced mPGES-1 expression or activity, e.g. heat, swelling, pain, redness, dilation of blood vessels and/or increased blood flow.

The term "inflammation" is also understood to include any inflammatory disease, disorder or condition per se, any condition that has an inflammatory component associated with it, and/or any condition characterized by inflammation as a symptom, including, inter alia, acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever.

In a preferred embodiment, the compounds of the invention are used in methods for treating, preventing, or suppressing symptoms associated with enhanced mPGES-1 expression or activity, which symptoms at least include one or more of inflammation, pain, swelling, fever, angiogenesis and anorexia.

Preferably, the compounds of the invention are used in methods for in treating, preventing, or suppressing symptoms of diseases or conditions that involve (enhanced expression and/or activity of) PGES-1, that are associated with mPGES-1, and of diseases or conditions on which effectiveness of the compounds is expected based on analgesic, anti-inflammatory, anti-angiogenic cytostatic and/or antipyretic action of inhibition of mPGES-1.

The compounds of the invention are therefore preferably used for preventing or suppressing symptoms mediated by enhanced mPGES-1 expression or activity in the treatment of a disease or condition selected from the group consisting of: a) acute and chronic inflammation; skin diseases such as dermatitis, eczema, psoriasis, burns, acne vulgaris, hidradenitis suppurativa and tissue trauma; visceral diseases such as inflammatory bowel disease, Crohn's disease, ulcerative colitis, diverticulitis, irritable bowel disease (IBS), peptic ulcers, cystitis, (chronic) prostatitis, pancreatitis or nephritis; ear, nose, mouth and throat disease such as influenza, rhinitis, pharyngitis, tonsillitis, conjunctivitis, iritis, scleritis, otitis and uveitis; viral and bacterial infections; inflammation related anorexia; an allergy; pelvic inflammatory disease; reperfusion injury; transplant rejection; tendinitis, vasculitis and phlebitis; b) acute pain, chronic pain, neuropathic pain, nociceptive pain, hyperalgesia, pain related to central sensitization, allodynia inflammatory pain, visceral pain, cancer pain, trauma pain, dental or surgery pain, postoperative pain, delivery pain, childbirth ache, persistent pain, peripheral mediated pain, central mediated pain, chronic headache, migraine, sinus headaches, tension headaches, phantom limb pain, peripheral nerve injury chemotherapy pain, and cancer pain; c) an autoimmune disease such as arthritis, osteoarthritis, juvenile arthritis, rheumatoid arthritis, ankylosing spondylitis, gout, rheumatic fever, bursitis, systemic lupus erythematosus (SLE) and multiple sclerosis; d) a breathing disorder or lung disease such as asthma, chronic obstructive pulmonary disease (COPD), sarcoidosis and pulmonary fibrosis; e) a cancer such as brain cancer, prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma and skin B-cell lymphoma; f) diabetic complications include diabetic vasculopathy, diabetic neuropathy and diabetic retinopathy; g) a neurodegenerative disorder such as Alzheimer's disease, Parkinson's disease, Huntington's disease and amyotrophic lateral sclerosis; and, h) a cardiovascular disease such as atherosclerosis, thrombosis, stroke and coronary heart disease.

In another embodiment, the invention relates to a method for treating a disease or condition mediated by or associated with enhanced mPGES-1 expression or activity, wherein the method comprises the step of administering to a subject suffering from the disease or condition an effective amount of a compound of the invention. The disease or condition mediated by or associated with enhanced mPGES-1 expression or activity preferably is selected from the group consisting of a) acute and chronic inflammation; skin diseases such as dermatitis, eczema, burns, acne vulgaris, hidradenitis suppurativa and tissue trauma; visceral diseases such as ulcerative colitis, diverticulitis, irritable bowel disease (IBS), peptic ulcers, cystitis, (chronic) prostatitis or nephritis; ear, nose, mouth and throat disease such as influenza, rhinitis, pharyngitis, tonsillitis, conjunctivitis, iritis, scleritis, otitis and uveitis; viral and bacterial infections; inflammation related anorexia; an allergy; pelvic inflammatory disease; transplant rejection; tendinitis, vasculitis and phlebitis; b) acute pain, chronic pain, neuropathic pain, nociceptive pain, hyperalgesia, pain related to central sensitization, allodynia inflammatory pain, visceral pain, cancer pain, trauma pain, dental or surgery pain, postoperative pain, delivery pain, childbirth ache, persistent pain, peripheral mediated pain, central mediated pain, chronic headache, migraine, sinus headaches, tension headaches, phantom limb pain, peripheral nerve injury chemotherapy pain, and cancer pain; c) ankylosing spondylitis, gout, rheumatic fever, bursitis; and d) diabetic complications include diabetic vasculopathy, diabetic neuropathy and diabetic retinopathy.

An "effective amount" of a compound is an amount of a compound which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

The "effective amount" of that may be combined with the carrier materials to produce a single dosage form will vary depending upon the host to which the active ingredient is administered and the particular mode of administration. The unit dosage chosen is usually fabricated and administered to provide a desired final concentration of the compound in the blood.

The effective amount (i.e. the effective total daily dose), preferably for adults, is herein defined as a total daily dose of about 5 to 2000 mg, or about 10 to 1000 mg, or about 20 to 800 mg, or about 30 to 800 mg or about 30 to 700 mg, or about 20 to 700 mg or about 20 to 600 mg, or about 30 to 600 mg, or about 30 to 500 mg, about 30 to 450 mg or about 30 to 400 mg, or about 30 to 350 mg or about 30 to 300 mg or about 50 to 600 mg, or about 50 to 500 mg, or about 50 to 450 mg, or about 50 to 400 mg or about 50 to 300 mg, or about 50 to 250 mg, or about 100 to 250 mg or about 150 to 250 mg. In the most preferred embodiment, the effective amount is about 200 mg.

Alternatively, the effective amount of the compound, preferably for adults, preferably is administered per kg body weight. The total daily dose, preferably for adults, is therefore about 0.05 to about 40 mg/kg, about 0.1 to about 20 mg/kg, about 0.2 mg/kg to about 15 mg/kg, or about 0.3 mg/kg to about 15 mg/kg or about 0.4 mg/kg to about 15 mg/kg or about 0.5 mg/kg to about 14 mg/kg or about 0.3 mg/kg to about 14 mg/kg or about 0.3 mg/kg to about 13 mg/kg or about 0.5 mg/kg to about 13 mg/kg or about 0.5 mg/kg to about 11 mg/kg.

The total daily dose for children is preferably at most 200 mg. More preferably the total daily dose is about 5 to 200 mg, about 10 to 200 mg, about 20 to 200 mg about 30 to 200 mg about 40 to 200 mg, or about 50 to 200 mg. Preferably, the total daily dose for children is about 5 to 150 mg, about 10 to 150 mg, about 20 to 150 mg about 30 to 150 mg about 40 to 150 mg, or about 50 to 150 mg. More preferably, the total daily dose is about 5 to 100 mg, about 10 to 100 mg, about 20 to 100 mg about 30 to 100 mg about 40 to 100 mg, or about 50 to 100 mg. Even more preferably, the total daily dose is about 5 to 75 mg, about 10 to 75 mg, about 20 to 75 mg about 30 to 75 mg about 40 to 75 mg, or about 50 to 75 mg.

Alternative examples of dosages which can be used are an effective amount of the compounds of the invention within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight.

Compounds of the present invention may be administered in a single daily dose, or the total daily dosage may be administered in divided dosage of two, three or four times daily.

In a preferred embodiment of the invention, "subject", "individual", or "patient" is understood to be an individual organism, preferably a vertebrate, more preferably a mammal, even more preferably a primate and most preferably a human.

The dose as defined herein is preferably suitable for administration to humans. Hence, in a preferred embodiment, the invention pertains to a compound as defined herein above, for use in treating, preventing, or suppressing symptoms associated with enhanced mPGES-1 expression or activity by administration of an effective dose as defined herein, wherein the subject to be treated is a primate, wherein preferably the subject is a human.

In a further preferred embodiment of the invention, the human is an adult, e.g. a person that is 18 years or older. In addition, it is herein understood that the average weight of an adult person is 62 kg, although the average weight is known to vary between countries. In another embodiment of the invention the average weight of an adult person is therefore between about 50-90 kg. It is herein understood that the effective dose as defined herein is not confined to subjects having an average weight. Preferably, the subject has a BMI (Body Mass Index) between 18.0 to 40.0 kg/m², and more preferably a BMI between 18.0 to 30.0 kg/m².

Alternatively, the subject to be treated is a child, e.g. a person that is 17 years or younger. In addition, the subject to be treated may be a person between birth and puberty or between puberty and adulthood. It is herein understood that puberty starts for females at the age of 10-11 years and for males at the age of 11-12 year. Furthermore, the subject to be treated may be a neonate (first 28 days after birth), an infant (0-1 year), a toddler (1-3 years), a preschooler (3-5 years); a school-aged child (5-12 years) or an adolescent (13-18 years).

A compound for use as defined herein (i.e. for use in treating, preventing, or suppressing symptoms mediated by or associated with enhanced mPGES-1 expression or activity by administration of an effective total daily dose) may be administered as a composition.

The compositions comprising the compounds as described above, can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote cerebral health or to prevent or halt the progression of a neurodegenerative disease associated with enhanced mPGES-1 expression or activity.

The subject compositions thus may be compounded with other physiologically acceptable materials that can be ingested including, but not limited to, foods. In addition or alternatively, the compositions for use as described herein may be administered orally in combination with (the separate) administration of food.

The compositions may be administered alone or in combination with other pharmaceutical or cosmetic agents and can be combined with a physiologically acceptable carrier thereof. In particular, the compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003), $21^{st}$ edition (2005) and $22^{nd}$ edition (2012), incorporated herein by reference.

Pharmaceutical or cosmetic compositions containing the compounds for use according to the invention may be in any form suitable for the intended method of administration, including, for example, a solution, a suspension, or an emulsion. In a preferred embodiment, the compound is administered in a solid form or in a liquid form.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water or saline. Such compositions may also comprise adjuvants, such as wetting agents, emulsifying and suspending agents, cyclodextrins, and sweetening, flavoring, and perfuming agents.

Liquid carriers are typically used in preparing solutions, suspensions, and emulsions. In a preferred embodiment, liquid carriers/liquid dosage forms contemplated for use in the practice of the present invention include, for example, water, saline, pharmaceutically acceptable organic solvent(s), pharmaceutically acceptable oils or fats, and the like, as well as mixtures of two or more thereof. In a preferred embodiment, the compound for use as defined herein is admixed with an aqueous solution prior to administration. The aqueous solution should be suitable for administration and such aqueous solutions are well known in the art. It is further known in the art that the suitability of an aqueous solution for administration may be dependent on the route of administration.

In a preferred embodiment, the aqueous solution is an isotonic aqueous solution. The isotonic aqueous solution preferably is almost (or completely) isotonic to blood plasma. In an even more preferred embodiment, the isotonic aqueous solution is saline.

The liquid carrier may contain other suitable pharmaceutically acceptable additives such as solubilizers, emulsifiers, nutrients, buffers, preservatives, suspending agents, thickening agents, viscosity regulators, stabilizers, flavorants and the like. Preferred flavorants are sweeteners, such as monosaccharides and/or disaccharides. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like.

For parenteral administration, the carrier can also be an oily ester such as ethyl oleate, isopropyl myristate, and the like. Compositions for use in the present invention may also be in the form of microparticles, microcapsules, liposomal encapsulates, and the like, as well as combinations of any two or more thereof.

Time-release, sustained release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound as defined herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.Y., p. 33 et seq (1976).

A pharmaceutical or cosmetic composition can comprise a unit dose formulation, where the unit dose is a dose sufficient to have a therapeutic or suppressive effect of a disorder or condition as defined herein. The unit dose may be sufficient as a single dose to have a therapeutic or suppressive effect of a disorder or condition as defined herein. Alternatively, the unit dose may be a dose administered periodically in a course of treatment or suppression of a disorder or condition as defined herein. During the course of the treatment, the concentration of the subject compositions may be monitored to insure that the desired level of the compound of the invention is maintained.

In a preferred embodiment the invention pertains to a compound as defined herein for use in treating, preventing, or suppressing symptoms mediated by or associated with enhanced mPGES-1 expression or activity by administration of an effective total daily dose, and wherein preferably the compound reaches a blood steady state level within 5 days. More preferably steady state levels are reached within 4 days, even more preferably within 3 days and most preferably steady state levels are reached within 2 days after the first administration.

Steady state is herein understood that the overall intake of a compound as defined above is (roughly) in dynamic equilibrium with its elimination. During steady state, the plasma levels of the compound preferably maintained within the effective therapeutic range. Put differently, the levels of the compound in the blood are maintained between the minimum therapeutically effective concentration and the maximum therapeutically effective concentration. Below the minimum concentration, the compound does not have sufficient therapeutic effect to be considered efficacious. Above the maximum concentration, side effects increase eventually leading to toxicity.

To maintain an effective therapeutic range during treatment, the average plasma concentrations ($C_{av}$) of the compound as defined herein is maintained between about 10 ng/ml to about 20000 ng/ml, or about 20 ng/ml to about 10000 ng/ml, or about 30 ng/ml to about 5000 ng/ml, or between about 30 ng/ml to about 4000 ng/ml, or between about 30 ng/ml to about 3000 ng/ml, or between about 30 ng/ml to about 2000 ng/ml, or about 30 ng/ml to about 1000 ng/ml, or between about 50 ng/ml to about 5000 ng/ml, or between about 100 ng/ml to about 5000 ng/ml, or between about 50 ng/ml to about 4000 ng/ml, or between about 50 ng/ml to about 3000 ng/ml, or between about 50 ng/ml to about 2000 ng/ml, or between about 50 ng/ml to about 1000 ng/ml. In a more preferred embodiment, the average plasma concentration of the compound is maintained between about 50 ng/ml-500 ng/ml or 100 ng/ml-500 ng/ml.

The average plasma concentrations may be determined using any conventional method known in the art. However in a preferred embodiment, the plasma concentrations are determined by extracting the compound as defined herein from human plasma by protein precipitation, followed by Liquid Chromatography-Tandem Mass Spectrometry (LC-MS/MS). The concentration of the compound may subsequently be determined using calibration standards.

The compound as defined herein may be metabolized and instead of, or in addition to the non-metabolized compound, the effective therapeutic range of the metabolized compound may be maintained during treatment. In a preferred embodiment of the invention, the average plasma concentrations ($C_{av}$) of the metabolized compound is maintained between about 5 ng/ml to about 5000 ng/ml, or about 10 ng/ml to about 2000 ng/ml, or about 20 ng/ml to about 1000 ng/ml, or between about 20 ng/ml to about 800 ng/ml, or between about 20 ng/ml to about 600 ng/ml, or between about 20 ng/ml to about 400 ng/ml, or about 20 ng/ml to about 200 ng/ml, or between about 30 ng/ml to about 1000 ng/ml, or between about 50 ng/ml to about 1000 ng/ml, or between about 30 ng/ml to about 800 ng/ml, or between about 30 ng/ml to about 600 ng/ml, or between about 30 ng/ml to about 400 ng/ml, or between about 30 ng/ml to about 200 ng/ml. In a more preferred embodiment, the average plasma concentration of the compound is maintained between about 40 ng/ml-500 ng/ml or 50 ng/ml-200 ng/ml.

During or after administration of the compound as defined herein, the maximum plasma concentrations ($C_{max}$) remain below about 20000 ng/ml or below 10000 ng/ml or below 5000 ng/ml or below about 4000 ng/ml or below about 3000 ng/ml or below about 2000 ng/ml or below about 1000 ng/ml. In the most preferred embodiment, the maximum plasma concentrations remain below about 500 ng/ml.

Similarly, the maximum plasma concentrations of the metabolized compound remain below about 5000 ng/ml, or 2000 ng/ml, or 1000 ng/ml, or below about 800 ng/ml or below about 600 ng/ml or below about 400 ng/ml. In the most preferred embodiment, the maximum plasma concentrations of the metabolized compound remain below about 250 ng/ml.

To maintain an effective range during treatment, the compound may be administered once a day, or once every two, three, four or five days. However preferably, the compound may be administered at least once a day. Hence in a preferred embodiment, the invention pertains to a compound as defined herein above, for use in treating, preventing, or suppressing symptoms mediated by or associated with enhanced mPGES-1 expression or activity by administration of an effective total daily dose, wherein the effective dose is defined herein above. The total daily dose may be administered as a single daily dose. Alternatively, the compound is administered at least twice daily. Hence, the compound as defined herein may be administered once, twice, three, four or five times a day. As such, the total daily dose may be divided over the several doses (units) resulting in the administration of the total daily dose as defined herein. In a preferred embodiment, the compound is administered twice daily. It is further understood that the terms "twice daily", "bid" and "bis in die" can be used interchangeable herein.

In a preferred embodiment, the total daily dose is divided over several doses per day. These separate doses may differ in amount. For example for each total daily dose, the first dose may have a larger amount of the compound than the second dose or vice versa. However preferably, the compound is administered in similar or equal doses. Therefore in a most preferred embodiment, the compound is administered twice daily in two similar or equal doses.

In a further preferred embodiment of the invention, the total daily dose of the compound as defined herein above is administered in at least two separate doses. The interval between the administration of the at least two separate doses is at least about 0.5, 1, 2, 3, 4, 5, 6, 7, 8, 9, 10, 11 or 12 hours, preferably the interval between the at least two separate doses is at least about 4, 5, 6, 7, 8, 9, 10, 11 or 12 hours and more preferably the interval between the at least two separate doses is at least about 8, 9, 10, 11 or 12 hours.

The composition can be administered in an effective total daily dose as defined herein, either as a prophylaxis or treatment, to a patient in any of a number of methods. In particular, the method of administration can vary based on the individual subject, the condition or the stage of disease, and other factors evident to one skilled in the art.

The compounds for a use as defined herein may be administered enterally, orally, parenterally, sublingually, by inhalation (e. g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds are mixed with pharmaceutically acceptable carriers, adjuvants, and vehicles appropriate for the desired route of administration. Oral administration is a preferred route of administration, and formulations suitable for oral administration are preferred formulations. Alternatively, the compounds may be administered by supplementation via gastric or percutaneous tubes.

Hence, in a preferred embodiment the invention pertains to a compound as defined herein above, for use in treating, preventing, or suppressing symptoms mediated by or associated with enhanced mPGES-1 expression or activity by administration of an effective total daily dose, wherein compound is administered orally.

The oral route is the preferred means of administration and (at least for adults) preferably the dosage form used is a solid oral dosage form. The class of solid oral dosage forms consists primarily of tablets and capsules, although other forms are known in the art and can be equally suitable. When used as a solid oral dosage form, the compound as defined herein may e.g. be administered in the form of an immediate release tablet (or a capsule and the like) or a sustained release tablet (or a capsule and the like). Any suitable immediate release or sustained release solid dosage forms can be used in the context of the invention as will be evident for the skilled person.

The compounds described for use as described herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at room temperature but liquid at the rectal temperature and will therefore melt in the rectum and release the drug.

While the compounds for use as described herein can be administered as the sole active pharmaceutical (or cosmetic) agent, they can also be used in combination with one or more other agents used in the treatment or suppression of disorders.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

EXAMPLES

Example 1

Figure 1:
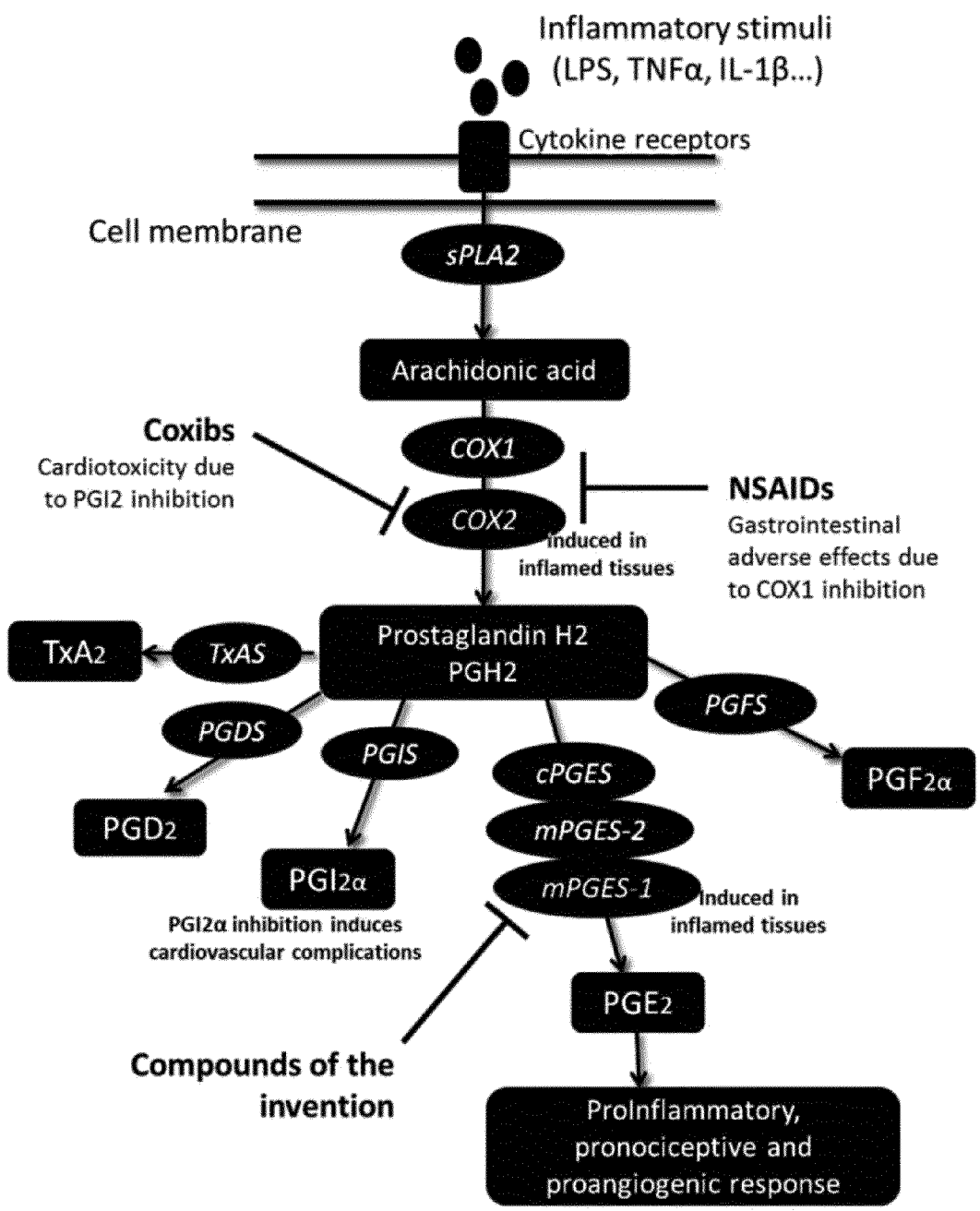
FIG. 1. Synthesis pathways of prostaglandins and the targeting strategies.

Methods and Materials
Chemicals and Antibodies

Antibodies directed against cPGES, mPGES-1 and mPGES-2 were purchased from Cayman chemicals. Antibodies directed against COX-1, COX-2 and Actin were purchased from R&D systems, Thermo Fisher Scientific and Sigma-Aldrich, respectively. COX inhibitors, Celecoxib and Indomethacin, and Lipopolysaccharide were purchased from Sigma-Aldrich. mPGES-1 inhibitors, MK866 and PF9184, and $PGH_2$ were purchased from Cayman Chemicals. IL-1β was purchased at Cell Signaling Technologies.

Compounds for use according to the invention were prepared as described in WO2014/011047 or in WO2017/060432.

Raw 264.7 Cell Culture

RAW264.7 cells (Sigma-Aldrich, St-Louis) were maintained in DMEM (Thermo Fisher Scientific) containing 10% FBS (Greiner Bio-one), and antibiotics (100 U/ml penicillin, 100 µg/ml streptomycin) under a humidified atmosphere of 5% CO2 at 37° C. The cells were grown to 80% confluence, scraped and then cultured in either 96-well plates ($2 \times 10^4$ cells/well) or six-well plates ($4 \times 10^5$ cells/well) for 6-24 hours before an experiment.

Human Primary Skin Fibroblast Culture

The cells were maintained in M199, HEPES (Thermo Fischer Scientific) containing 10% FBS (#758093, Greiner Bio-one), 100 IU/ml penicillin and 100 µg/ml streptomycin (#30-002-CI, Corning) under a humidified atmosphere of 5% CO2 at 37° C. The cells were passaged by trypsinization every 4-5 days until they reached the passage number 20, and then discarded. The cells were grown to 80% confluence, trypsinized and then cultured in 96-well plates ($4 \times 10^3$ cells/well) 24 hours before an experiment.

Prostaglandins Quantification

The concentration of the $PGE_2$, $PGD_2$ and 6-keto-$PGF_{1\alpha}$ in culture medium was determined by Enzyme-Linked Immuno Sorbent Assay (ELISA) using, respectively, the $PGE_2$ high sensitivity EIA kit (Enzo Life Science), the Prostaglandin $D_2$-MOX ELISA Kit (Cayman Chemicals) and the 6-keto Prostaglandin $F_{1\alpha}$ ELISA Kit (Cayman Chemicals), according to the manufacturer's instructions. Samples (100 µl) of culture medium from each well were harvested and diluted with the assay buffer. The values of each prostanoid were calculated using a standard curve and normalized as indicated in the figure legends.

Western Blot Analysis

After treatment the cells were harvested by scrapping and lysed in radioimmunoprecipitation assay buffer (50 mM Tris-HCl pH8.0, 150 mM NaCl, 0.2% Triton, 1× protease inhibitor, and 0.1 mg/ml DNAse). The protein concentration of the samples was determined by Bradford assay. Equal amount of proteins of each samples were separated by SDS-polyacrylamide gel electrophoresis (SDS-PAGE) and electro-transferred to PVDF membrane. The membranes were blocked for 1 h at room temperature in Odyssey blocking buffer (Li-Cor), and then incubated with primary antibody against mPGES-1 (1:200 dilution), mPGES-2 (1:200 dilution), cPGES (1:200 dilution), COX-1 (1:250 dilution), COX-2 (1:500 dilution), or β-actin (1:10000 dilution) in TBST at 4° C. overnight. After washing the membranes three times with TBST, secondary antibody (Goat anti-Rabbit IgG (H+L) Secondary Antibody, Alexa Fluor 488 or Goat anti-Mouse IgG (H+L) Secondary Antibody, Alexa Fluor 647, Thermo Fisher scientific) was added at 1:10000 dilutions for 1 hour at room temperature. Fluorescence scanning of the blots was performed using an Odyssey Infrared Imaging System (Li-Cor).

Microsomal PGES Activity

PGES activity was measured by assessment of the conversion of $PGH_2$ to $PGE_2$. In brief, after 24 hours incubation with 1 μg/mL LPS the cells were harvested and lysed by sonication (three times for 10 seconds each, at 1 min intervals) in 300 μl of 1 M Tris-HCl (pH 8.0). After centrifugation of the lysate at 12,000 g for 10 min at 4° C., the supernatant was collected and further centrifuged at 100,000 g for 1 h at 4° C. The pellets (microsomal membranes) were resuspended in 100 μl of 0.1M Tris-HCl, pH 8.0, containing protease inhibitors) and subjected to measurement of microsomal PGES activity. For measurement of PGES activity, an aliquot of each sample equivalent to 50 μg of protein was incubated with 2 μg of $PGH_2$ for 60 s at 24° C. in 0.1 ml of 1 M Tris-HCl containing 2 mM glutathione (Sigma-Aldrich) and 14 μM indomethacin, in the absence or presence of the tested compounds. The reaction was terminated by the addition of 100 mM $FeCl_2$, and further incubated at 20-25° C. for 15 min. After centrifugation of the reaction mixture, the $PGE_2$ concentration in the supernatant was measured with the $PGE_2$ high sensitivity EIA kit (Enzo Life Science) according to manufacturer's instructions.

RNA Quantification by qRT-PCR

After 6 h of treatment with 1 μg/mL LPS, in the absence or presence of tested compounds, total RNA was isolated from the cells by Trizol reagent (Thermo Fisher Scientific). The RNA was transcribed into cDNA by first-strand cDNA synthesis kit (Thermo Fisher Scientific). The cDNA was denatured for 10 min at 95° C. Specific DNA fragments for COX-1, COX-2, mPGES-1, mPGES-2, cPGES, and PPIA were amplified by PCR with SYBR Green (Roche Life Science) Cycler for 40 cycles with 15 s at 95° C., 60 s at 60° C. The oligonucleotide primers used for COX1 were 5'-GATTGTACTCGCACGGGCTAC-3' (forward) and 5'-GGATAAGGTTGGACCGCACT-3' (reverse), for COX2 were 5'-AGGACTCTGCTCACGAAGGA-3' (forward) and 5'-TGACATGGATTGGAACAGCA-3' (reverse), for mPGES-1 were 5'-AGCA CACTGCTGGTCATCAA-3' (forward) and 5'-CTCCACATCTGGGTCACTCC-3' (reverse), for mPGES-2 were 5'-GCTGGGGCTGTAC-CACAC-3' (forward) and 5'-GATTCACCTCCAC-CACCTGA-3' (reverse), for cPGES were 5'-GGTAGAGACCGCCGGAGT-3' (forward) and 5'-TCGTACCACTTTGCAGAAGCA-3' (reverse), for PPIA were 5'-AGGGTGGTGACTTTACACGC-3' (forward) and 5'-GATGCCAGGACCTGTATGCT-3' (reverse). The PCR amplifications were also carried out in samples without cDNA as negative controls. The relative gene expression of COX-1, COX-2, mPGES-1, mPGES-2, and cPGES was determined by the ΔΔCT method comparing expression in vehicle and treated groups. PPIA was used as a reference gene.

Results

Compound I-IVb-X Selectively Decreases the Level of $PGE_2$.

Figure 2A:
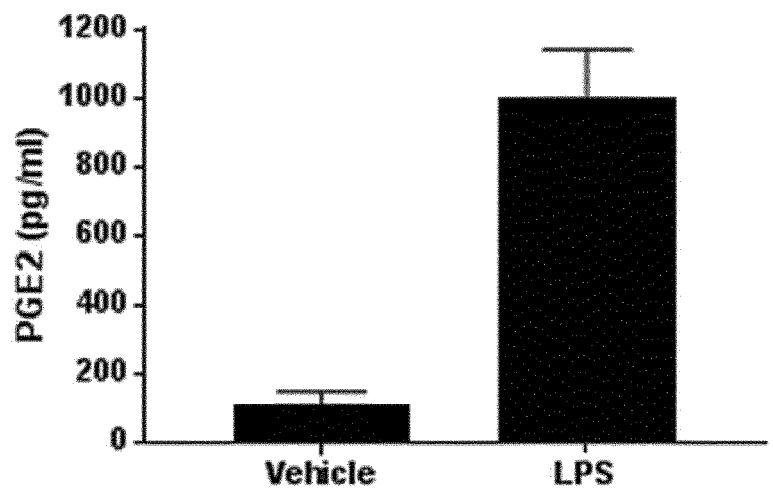
FIG. 2. (A-C) Levels of prostaglandins (PG) $PGE_2$ (A), $PGD_2$ (B) and 6-keto $PGF_{1\alpha}$ (C) in supernatant of RAW 264.7 murine macrophage cells exposed for 24 hours to vehicle or 1 µg/mL lipopolysaccharide (LPS), normalized on vehicle. (D-F) Levels of $PGE_2$, $PGD_2$ and 6-keto $PGF_{1\alpha}$ in supernatant of RAW 264.7 murine macrophage cells exposed for 24 hours to vehicle or 1 µg/mL LPS, alone (set as 100%) or in combination with increasing concentrations of compound I-IVb-X (a compound of general structure (I) wherein T is of general structure (IVb), in the S,R-configuration, and wherein as per compound X the following apply: $L=L^{19}$; $R^1$=H; $R^2$—$R^{2'}$=$L^3$; $R^3$=H; indicated as KH) (D), non-selective COX inhibitor indomethacin (E) or COX-2 inhibitor celecoxib (F).
Figure 2B:
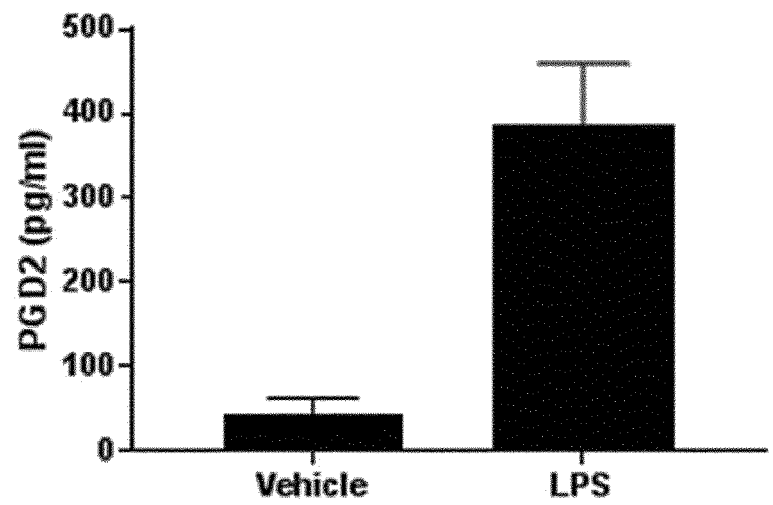
Figure 2C:
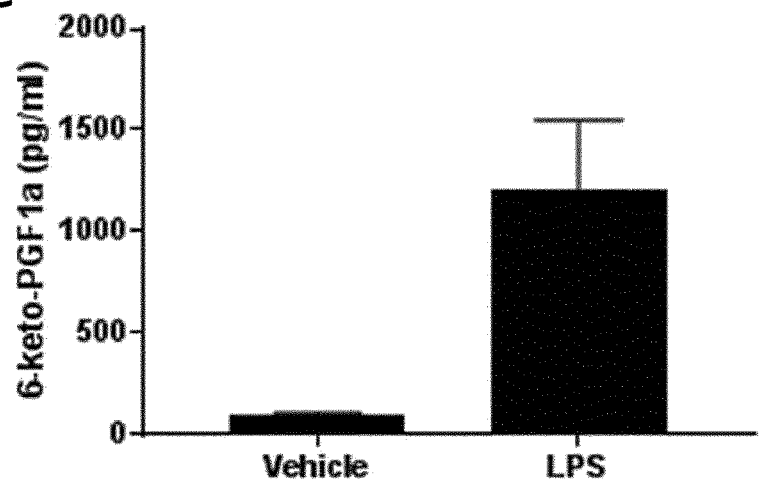
Figure 2D:
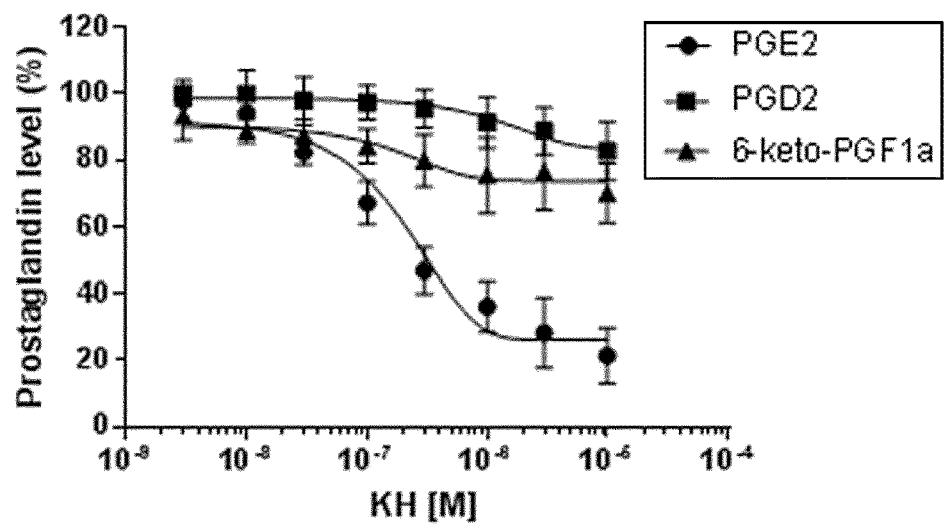
Figure 2E:
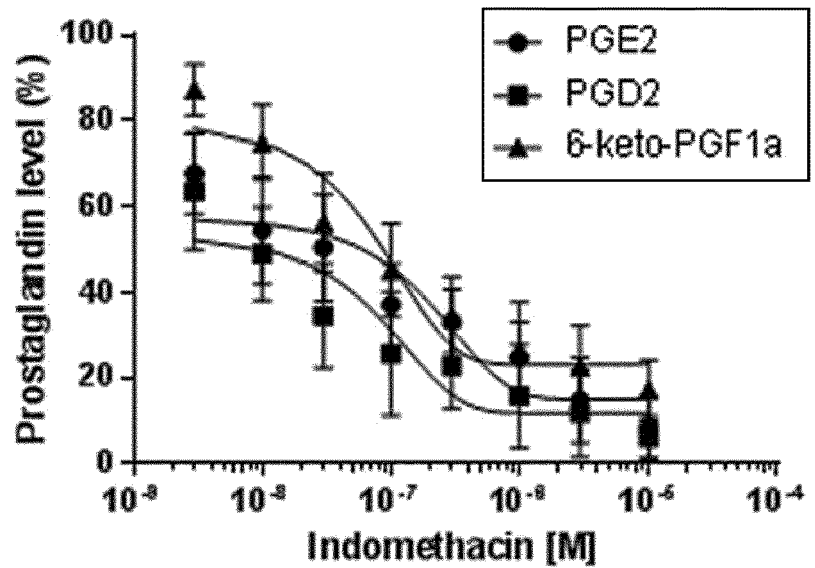
Figure 2F:
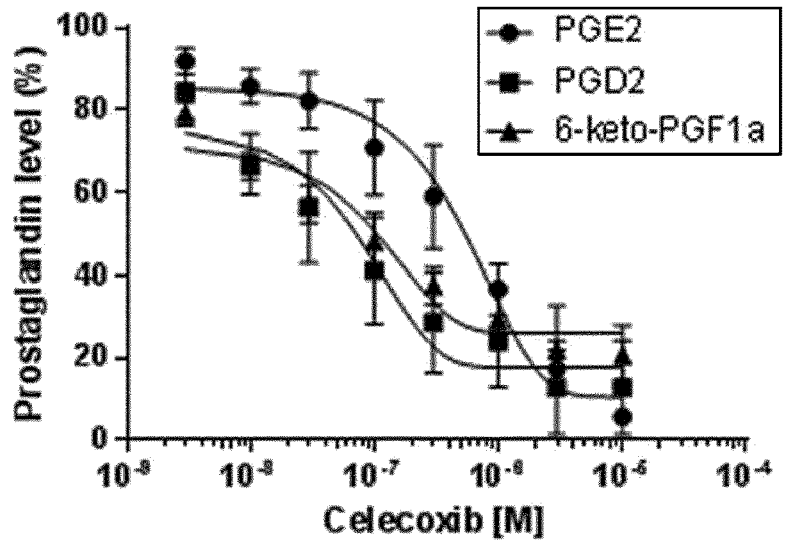
Figure 3A:
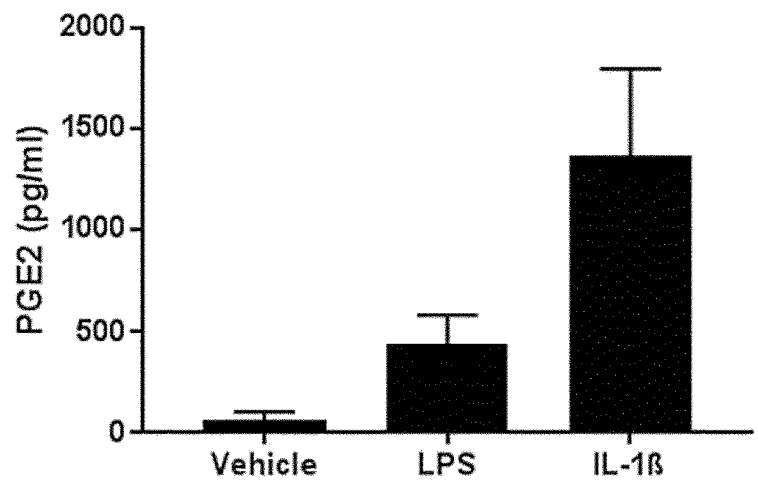
FIG. 3. (A-B) Levels of $PGE_2$ (A) and $PGD_2$ (B) in supernatant of human primary skin fibroblasts exposed for 24 hours to vehicle, 1 µg/mL LPS or 1 µg/mL Interleukin-1β (IL-1β), normalized on vehicle. (C-D) Levels of $PGE_2$ and $PGD_2$ in supernatant of human primary skin fibroblasts exposed for 24 hours to 1 µg/mL LPS (C) or 1 µg/mL IL-1β (D) alone (set as 100%) or in combination with increasing concentrations of compound I-IVb-X (indicated as KH).
Figure 3B:
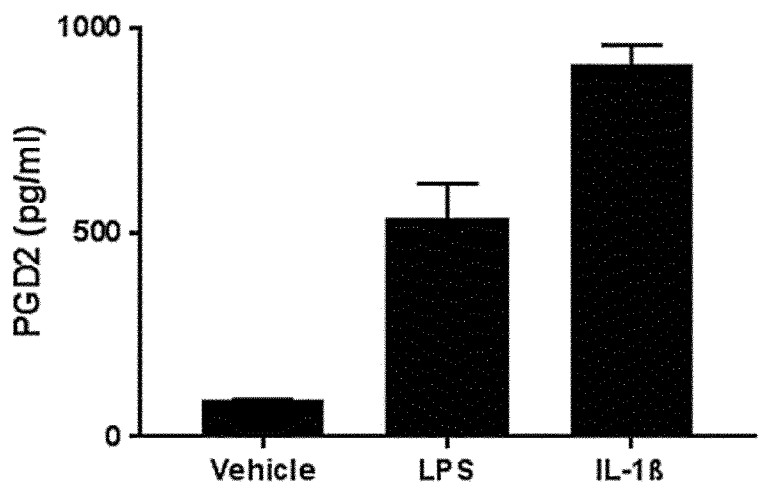
Figure 3C:
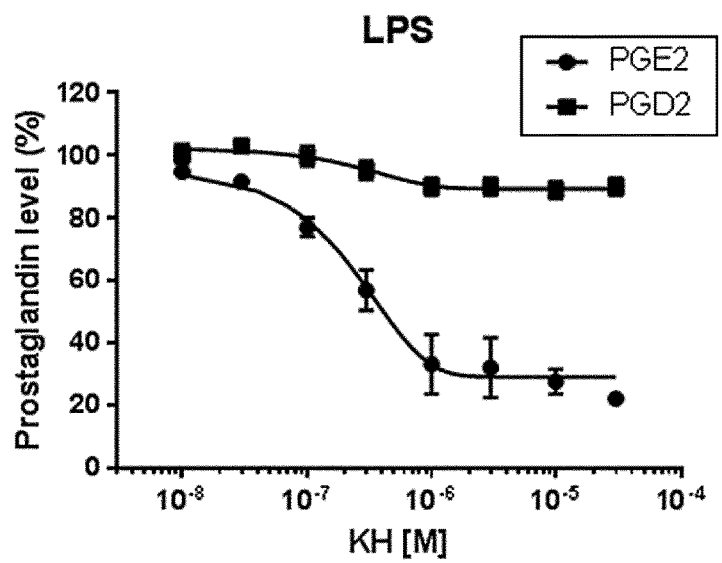
Figure 3D:
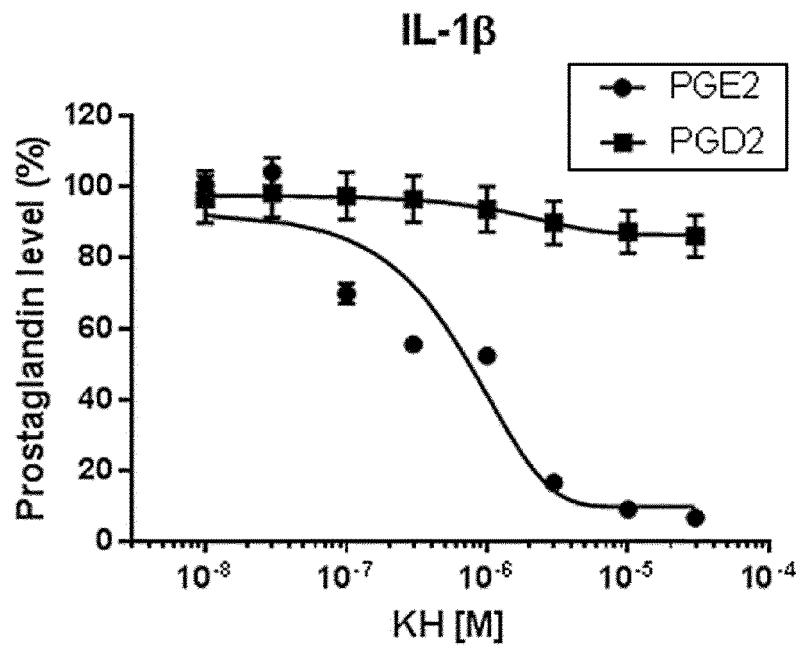

RAW 264.7 macrophage cells were treated with the inflammatory stimulus LPS alone or in combination with increasing concentrations of compound I-IVb-X (a compound of general structure (I) wherein T is of general structure (IVb), in the S,R-configuration, and wherein as per compound X the following apply: L=$L^{19}$; $R^1$=H; $R^2$=$R^{2'}$=$L^3$; $R^3$=H), the NSAID indomethacin or the Coxib Celecoxib. After 24 hours incubation the levels of $PGE_2$, $PGD_2$ and 6-keto $PGF_{1\alpha}$ were quantified in the cell supernatant by ELISA. As expected, LPS efficiently induced the production of the three prostaglandins (FIG. 2A-C) (Ikeda-Matsuo et al., 2005), which could all be dose-dependently reduced by the two COX inhibitors indomethacin and Celecoxib (FIG. 2E-F). Unexpectedly, while compound I-IVb-X could dose-dependently reduce the level of $PGE_2$ it has no effect on the two other prostaglandins $PGD_2$ and 6-keto $PGF_{1\alpha}$, a stable metabolite of $PGI_2$ commonly measured as a surrogate of $PGI_2$ (FIG. 2D). Similar results were obtained with compound I-IVb-X in human primary skin fibroblasts. After 24 hours incubation of fibroblast with either inflammatory stimulus LPS or IL-1β, $PGE_2$ and $PGD_2$ levels in the supernatant were strongly increased (FIGS. 3A&B). compound I-IVb-X could efficiently reduce the level of $PGE_2$, but not $PGD_2$, in supernatant of cells treated with either LPS (FIG. 3C) or IL-1β (FIG. 3D).

Compound I-IVb-X Selectively Decrease the Expression of mPGES-1 Enzyme.

Figure 4A:
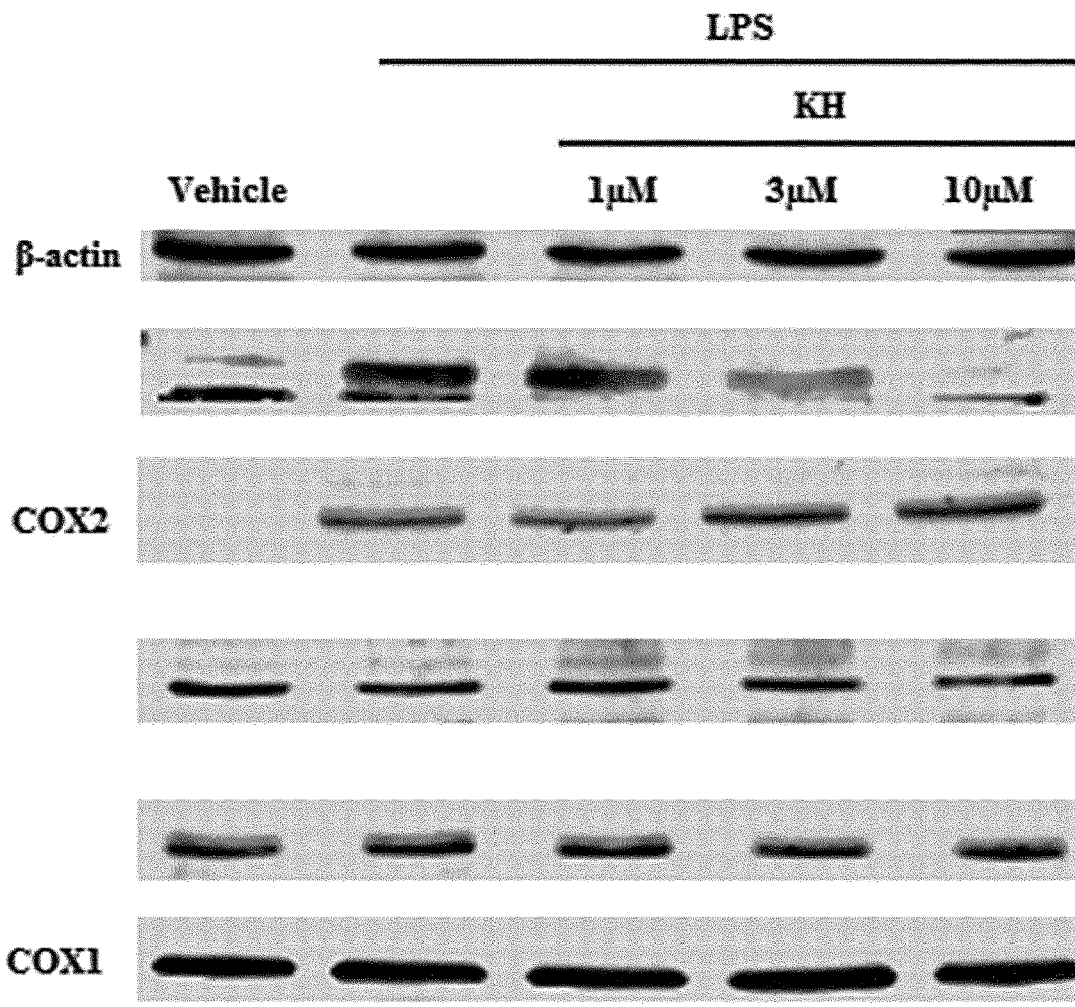
FIG. 4. (A) Western blot analysis of mPGES-1, COX-2, cPGES, mPGES-2, and COX-1 enzymes in RAW 264.7 murine macrophage cells exposed for 24 hours to vehicle or 1 µg/mL LPS, alone or in combination with increasing concentrations of compound I-IVb-X (indicated as KH). (B-F) Quantification of the levels of mPGES-1 (B), COX-2 (C), mPGES-2 (D), cPGES (E) and COX-1 (F) enzymes as in (A) with Actin as a loading reference and normalized to the vehicle treated cells.
Figure 4B:
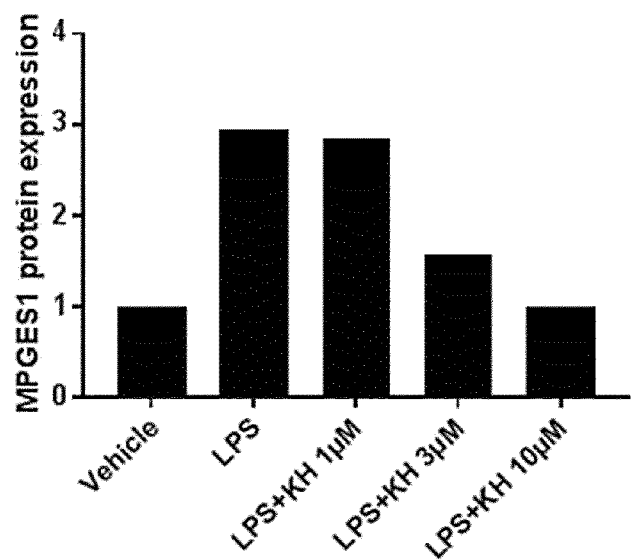
Figure 4C:
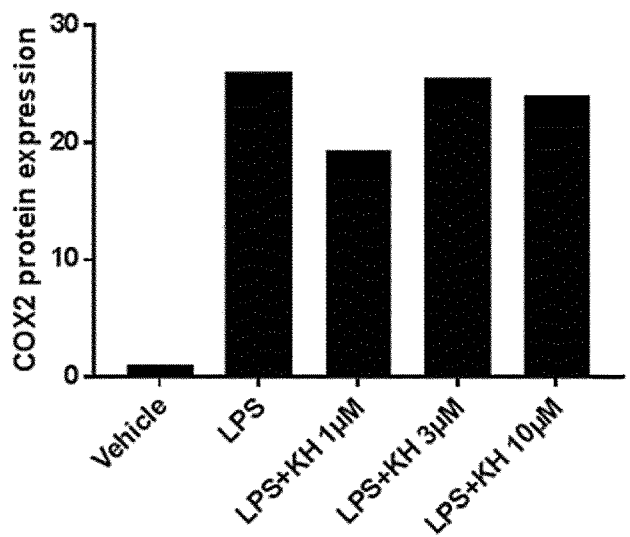
Figure 4D:
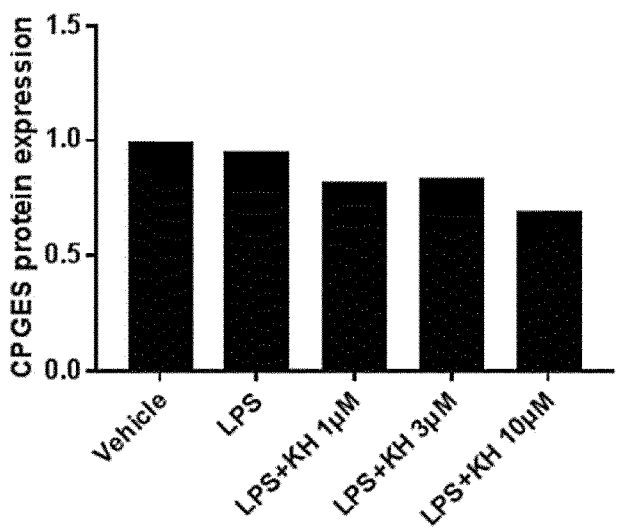
Figure 4E:
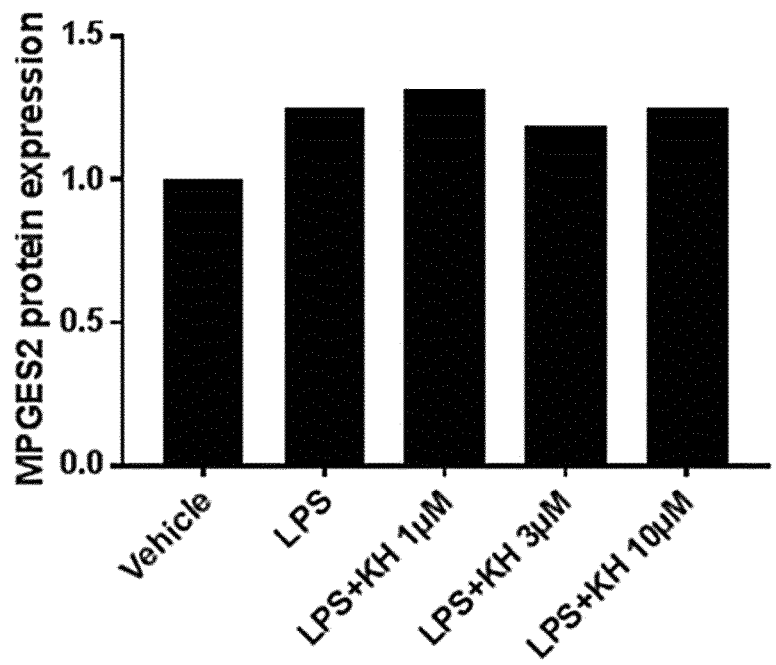
Figure 4F:
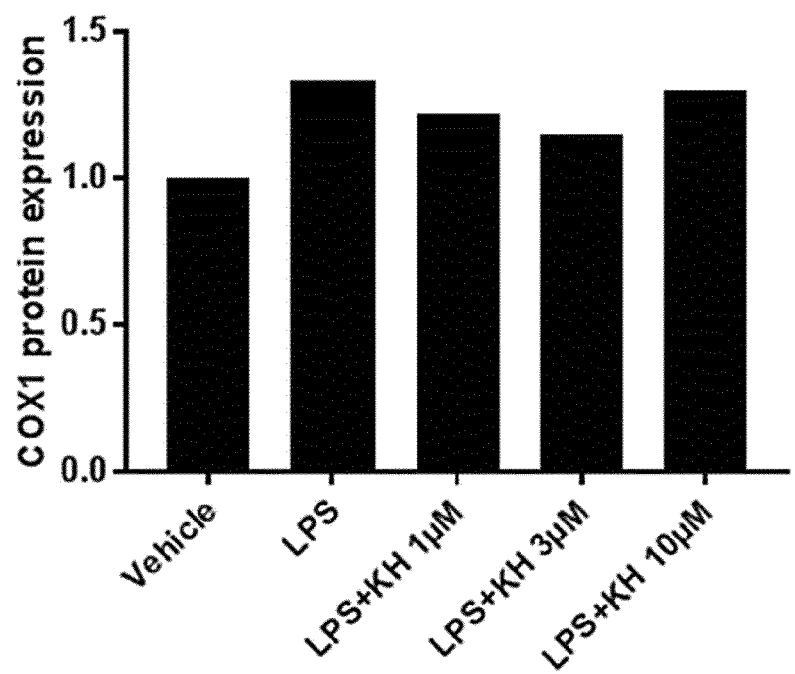
Figure 5A:
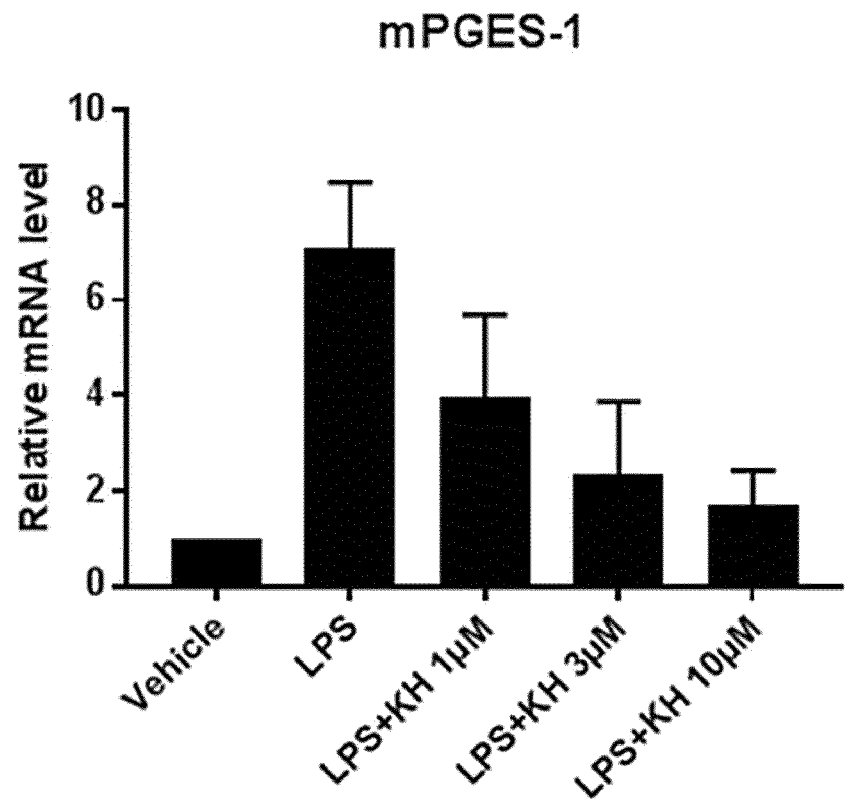
FIG. 5. Quantification by qPCR of the RNA levels of mPGES-1 (A), COX-2 (B), cPGES (C), mPGES-2 (D), and COX-1 (E) enzymes in RAW 264.7 murine macrophage cells exposed for 24 hours to vehicle, 1 µg/mL LPS alone or in combination with increasing concentrations of compound I-IVb-X (indicated as KH).
Figure 5B:
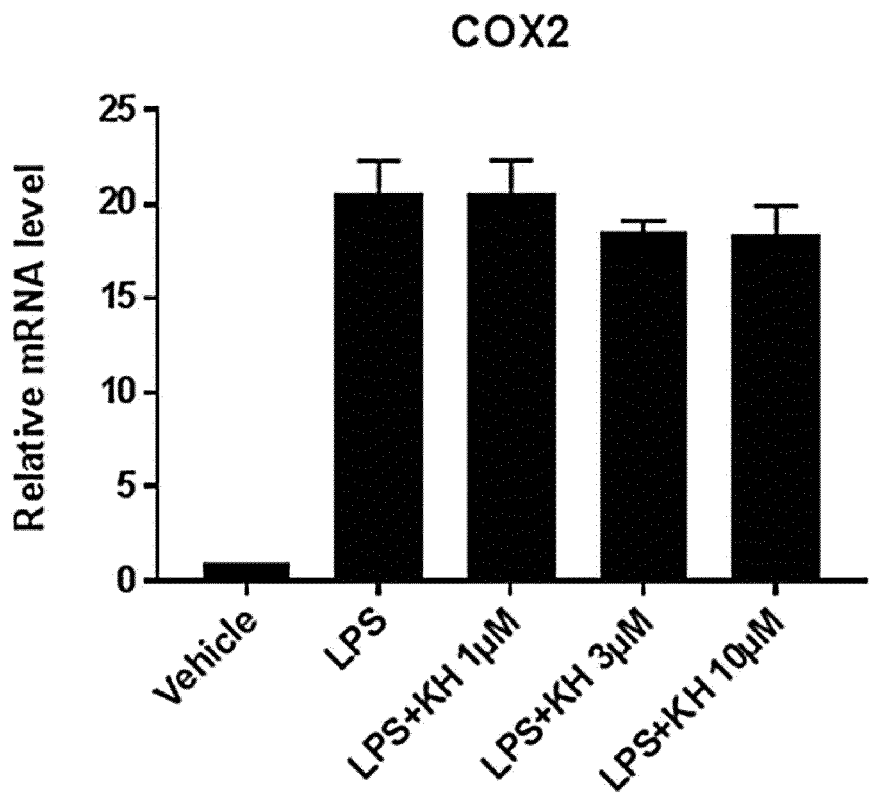
Figure 5C:
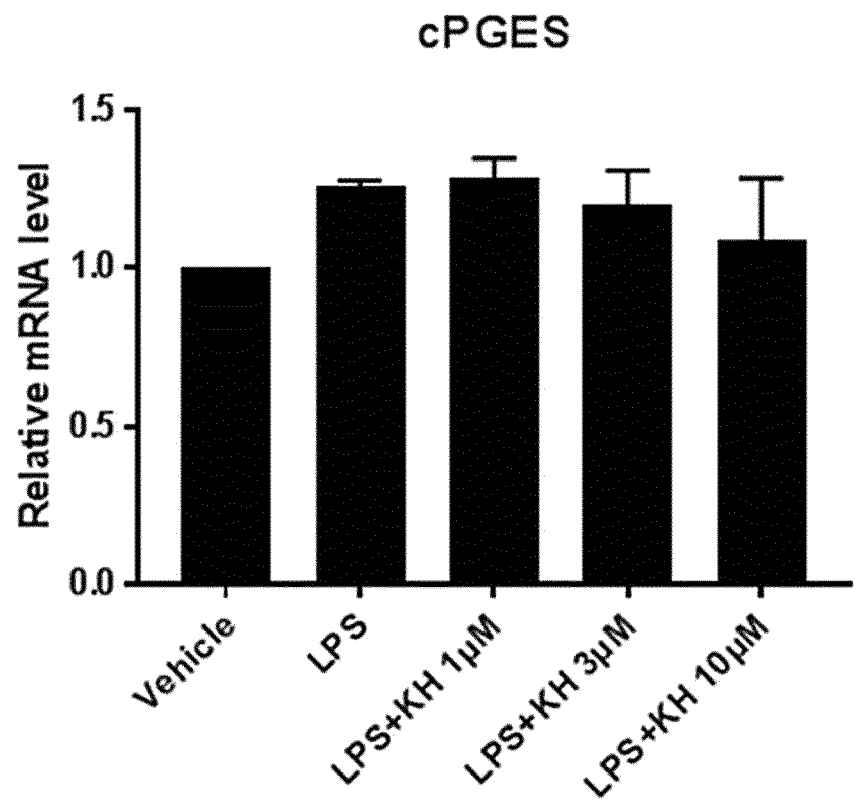
Figure 5D:
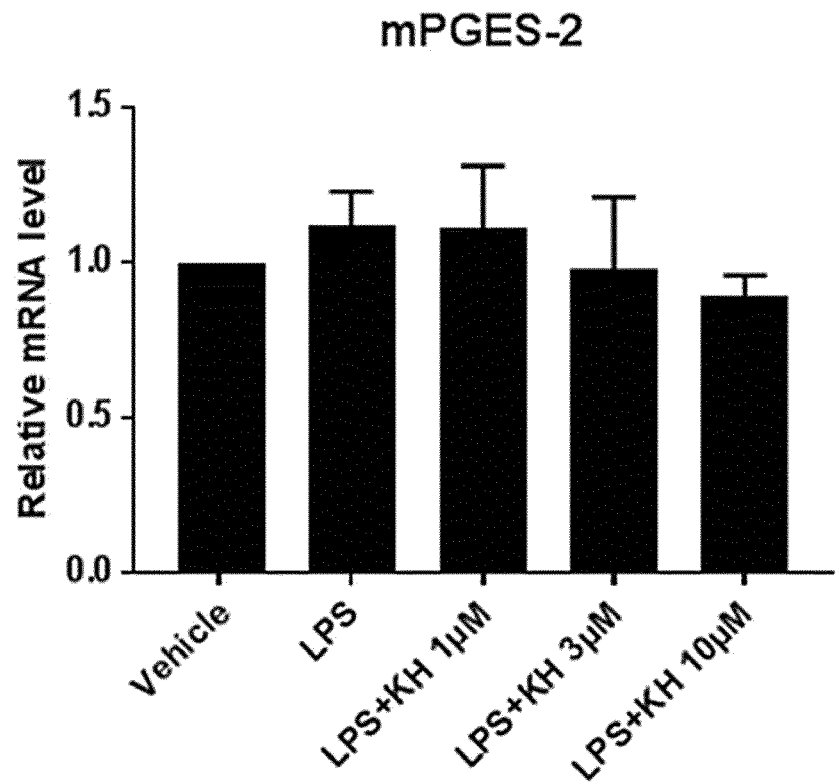
Figure 5E:
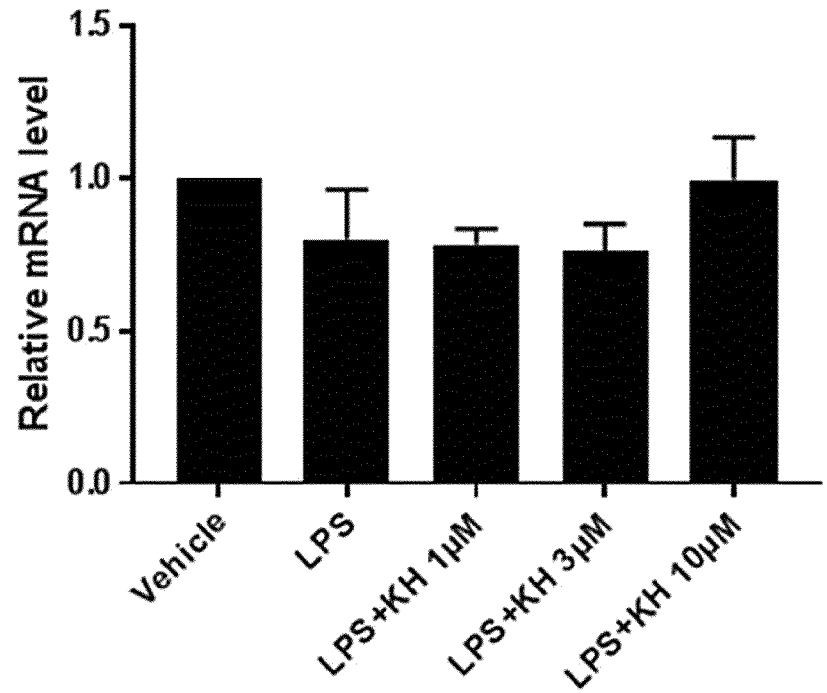

RAW 264.7 macrophage cells were treated with the inflammatory stimulus LPS alone or in combination with increasing concentrations of compound I-IVb-X. After 24 hours incubation the levels of mPGES-1, mPGES-2, cPGES, COX-1 and COX-2 proteins and RNA were quantified in the cells by western-blot or qPCR, respectively. As expected, LPS efficiently induced the expression of the two inducible enzymes mPGES-1 and COX-2 at the protein (FIGS. 4 A-C)) and RNA (FIGS. 5A&B) levels, while had no effect on constitutively expressed enzymes mPGES-2, cPGES and COX-1 at the protein (FIGS. 4A,D-F) and RNA (FIGS. 5 C-E) levels. While compound I-IVb-X could dose-dependently reduce the LPS-induced expression of mPGES-1 protein (FIG. 4B) and RNA (FIG. 5A), it had no effect on COX-2 expression (FIGS. 4C&5B). Compound I-IVb-X had no effect on the other three constitutive enzymes mPGES-2, cPGES and COX-1 (FIGS. 4 D-F and FIG. 5 C-E). These results show that compound I-IVb-X can selectively inhibit the expression of mPGES-1 enzyme induced by inflammatory stimulus LPS, which explain its selectivity in reducing solely $PGE_2$ and no other prostaglandins.

Compound I-IVb-X Inhibits mPGES-1 Enzyme Activity.

Figure 6A:
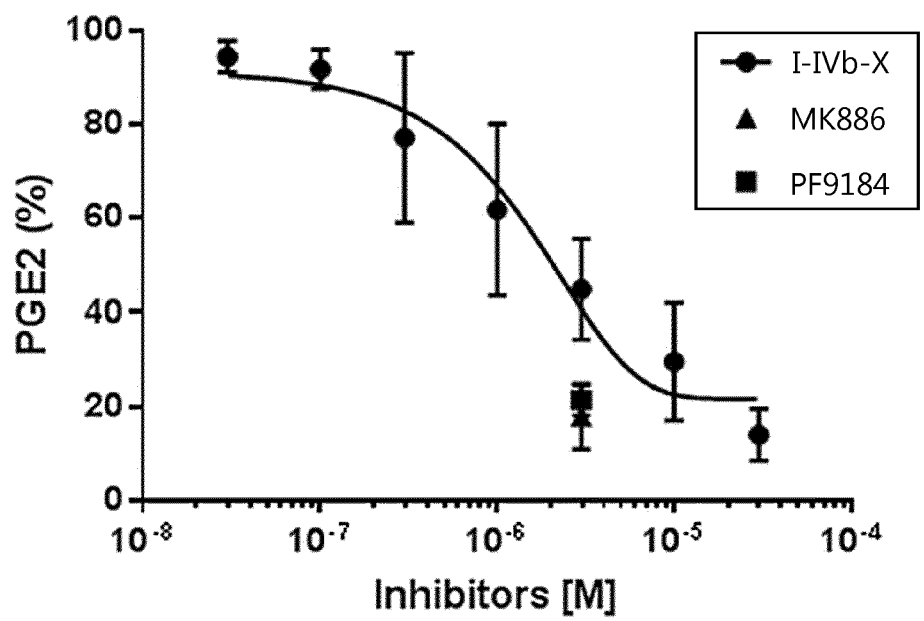
FIG. 6. mPGES-1 activity was assayed as conversion of $PGH_2$ to $PGE_2$ by microsomal fractions of RAW 264.7 cells treated for 24 hours with LPS 1 µg/mL to increase mPGES-1 expression. The microsomal fraction was exposed to increasing concentrations of compound to be tested, or 3 µM of know mPGES-1 inhibitors MK866 or PF9184 as positive controls. $PGE_2$ level was normalized on the vehicle treated microsomal samples (100%). (A) compound I-IVb-X; (B) compound I-IVb-AE; (C) compound I-IVb-A-HCl; (D) compound I-IVb-I.

RAW 264.7 macrophage cells were treated with the inflammatory stimulus LPS to increase the expression of mPGES-1. After 24 hours incubation the microsomes were isolated and exposed to increasing concentration of compound I-IVb-X or a single concentration of previously described mPGES-1 inhibitors MK866 and PF9184 for 30 minutes. The activity of mPGES-1 was then assayed in the microsomes fraction as the conversion of $PGH_2$ to $PGE_2$. The results show that mPGES-1 activity in purified microsomes treated with compound I-IVb-X or the two positive controls MK866 and PF9184 was decreased (FIG. 6A).

Example 2—Inhibition of mPGES-1 Enzyme Activity

Figure 6B:
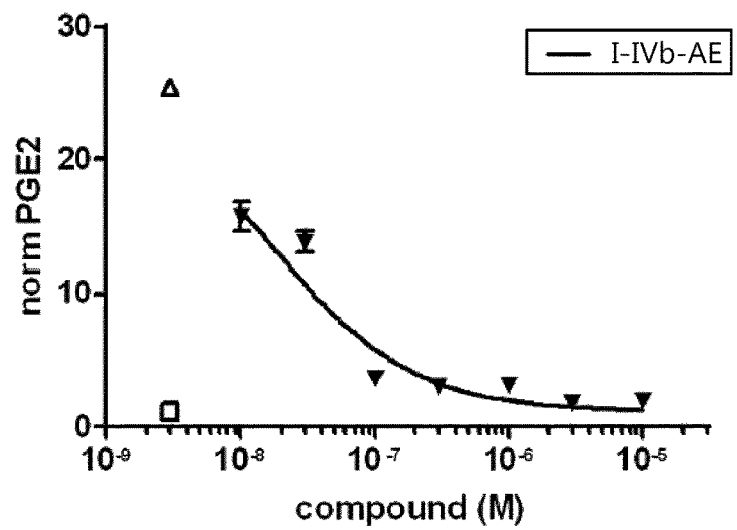
Figure 6C:
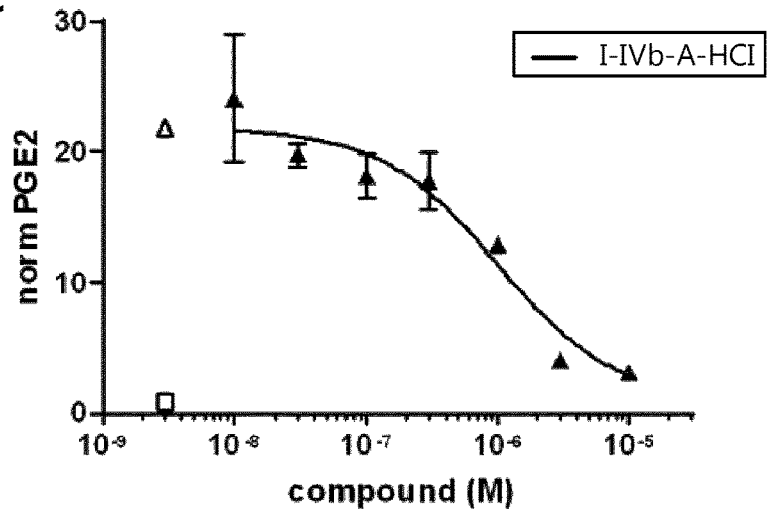
Figure 6D:
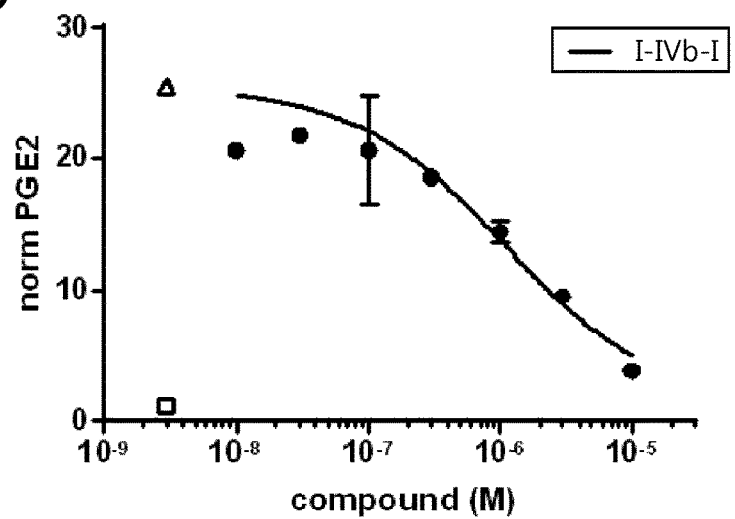

Using the methods as described in Example 1, additional compounds were tested. Table 1 provides an overview of the compounds that were tested, along with corresponding $IC_{50}$ values. FIGS. 6B, 6C, and 6D show corresponding inhibition curves for I-IVb-AE, I-IVb-A-HCl, and I-IVb-I, respectively.

TABLE 1

| Compound reference | Structure | Formula I wherein: | IC$_{50}$ (x10$^{-6}$) |
|---|---|---|---|
| | exemplary compounds that inhibit mPGES-1 enzyme activity | | |
| I-IVb-N | 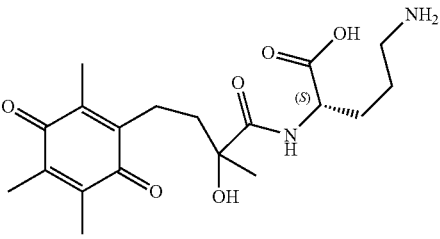 | T = IVb, N* = IIa<br>L = L$^{11}$, R$^1$ = H,<br>R$^2$ = H, R$^3$ = H | 0.01041 |
| I-IVb-AE | 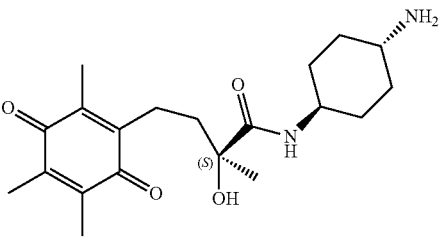 | T = IVb, N* = IIa<br>L = L$^{26}$, R$^1$ = H,<br>R$^2$ = H,<br>R$^5$—R$^{5'}$ = L$^1$,<br>R$^3$ = H | 0.01799 |
| I-IVb-AB-HCl | 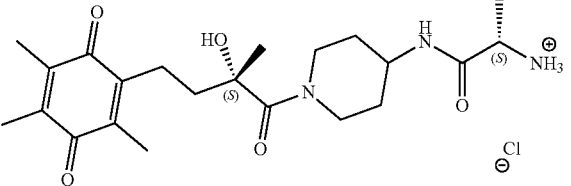 | T = IVb, N* = IIb<br>L = L$^{23}$,<br>R$^1$—R$^{1'}$ = L$^1$,<br>R$^2$ = H, R$^3$ = H<br>R$^4$ = H, X = Cl | 0.2381 |
| I-IVb-X | 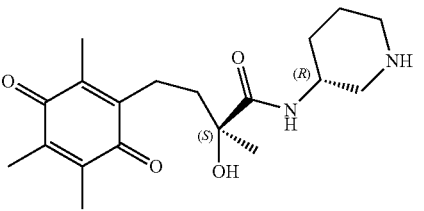 | T = IVb, N* = IIa<br>L = L$^{19}$, R$^1$ = H, R$^2$—R$^{2'}$ = L$^3$,<br>R$^3$ = H | 0.4579 |
| I-IVb-AI-HCl | 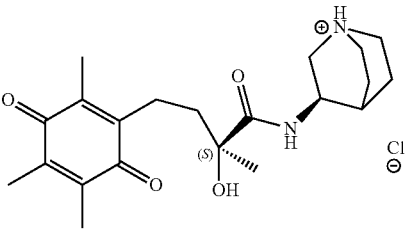 | T = IVb, N* = IIb<br>L = L$^{27}$, R$^1$ = H,<br>R$^2$—R$^{2'}$ = —CH$_2$—, R$^3$—R$^{3'}$ = L$^1$, R$^4$ = H, X = Cl | 0.7262 |
| I-IVb-A-HCl | 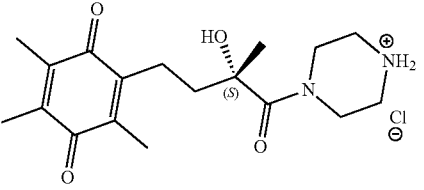 | T = IVb, N* = IIb<br>L = L$^1$, R$^1$—R$^2$ = L$^1$, R$^3$ = H, R$^4$ = H,<br>X = Cl | 1.024 |

TABLE 1-continued exemplary compounds that inhibit mPGES-1 enzyme activity

| Compound reference | Structure | Formula I wherein: | $IC_{50}$ $(\times 10^{-6})$ |
|---|---|---|---|
| I-IVb-AJ-HCl | [structure] | T = IVb, N* = IIb<br>L = $L^{28}$, $R^1$ = H, $R^2$ = H,<br>$R^3$ = H, $R^4$ = H, X = Cl | 1.05 |
| I-IVb-I | [structure] | T = IVb, N* = IIa<br>L = $L^1$, $R^1$ = H,<br>$R^2$ = Me, $R^3$ = Me | 1.118 |

REFERENCES

Akitake, Y., Nakatani, Y., Kamei, D., Hosokawa, M., Akatsu, H., Uematsu, S., et al. (2013). Microsomal prostaglandin E synthase-1 is induced in alzheimer's disease and its deletion mitigates alzheimer's disease-like pathology in a mouse model. J. Neurosci. Res. 91: 909-919.

Beales, I. L. P., and Ogunwobi, O. O. (2010). Microsomal prostaglandin E synthase-1 inhibition blocks proliferation and enhances apoptosis in oesophageal adenocarcinoma cells without affecting endothelial prostacyclin production. Int. J. Cancer 126: 2247-55.

Catella-Lawson, F., Mcadam, B., Morrison, B. W., Kapoor, S., Kujubu, D., Antes, L., et al. Effects of Specific Inhibition of Cyclooxygenase-2 on Sodium Balance, Hemodynamics, and Vasoactive Eicosanoids 1.

Chaudhry, U. A., Zhuang, H., Crain, B. J., and Doré, S. (2008). Elevated microsomal prostaglandin-E synthase-1 in Alzheimer's disease. Alzheimer's Dement. 4: 6-13.

Chen, Y., Liu, H., Xu, S., Wang, T., and Li, W. (2015). Targeting microsomal prostaglandin E 2 synthase-1 (mPGES-1): the development of inhibitors as an alternative to non-steroidal anti-inflammatory drugs (NSAIDs). Med. Chem. Commun. 6: 2081-2123.

Fahmi, H. (2004). mPGES-1 as a novel target for arthritis. Curr. Opin. Rheumatol. 16: 623-627.

Hanaka, H., Pawelzik, S.-C., Johnsen, J. I., Rakonjac, M., Terawaki, K., Rasmuson, A., et al. (2009). Microsomal prostaglandin E synthase 1 determines tumor growth in vivo of prostate and lung cancer cells. Proc. Natl. Acad. Sci. U.S.A. 106: 18757-62.

Hara, S., Kamei, D., Sasaki, Y., Tanemoto, A., and Nakatani, Y. (2010). Prostaglandin E synthases: Understanding their pathophysiological roles through mouse genetic models. Biochimie 92: 651-659.

Hui, Y., Ricciotti, E., Crichton, I., Yu, Z., Wang, D., Stubbe, J., et al. (2010). Targeted Deletions of Cyclooxygenase-2 and Atherogenesis in Mice. Circulation 121.

Ikeda-Matsuo, Y. (2017). The Role of mPGES-1 in Inflammatory Brain Diseases. Biol. Pharm. Bull 40: 557-563.

Ikeda-Matsuo, Y., Ikegaya, Y., Matsuki, N., Uematsu, S., Akira, S., and Sasaki, Y. (2005). Microglia-specific expression of microsomal prostaglandin E2 synthase-1 contributes to lipopolysaccharide-induced prostaglandin E2 production. J. Neurochem. 94: 1546-1558.

Kamei, D., Yamakawa, K., Takegoshi, Y., Mikami-Nakanishi, M., Nakatani, Y., Oh-Ishi, S., et al. (2004). Reduced pain hypersensitivity and inflammation in mice lacking microsomal prostaglandin e synthase-1. J. Biol. Chem. 279: 33684-95.

Kats, A., Båge, T., Georgsson, P., Jönsson, J., Quezada, H. C., Gustafsson, A., et al. (2013). Inhibition of microsomal prostaglandin E synthase-1 by aminothiazoles decreases prostaglandin E2 synthesis in vitro and ameliorates experimental periodontitis in vivo. FASEB J. 27: 2328-41.

Kim, S.-H., Hashimoto, Y., Cho, S.-N., Roszik, J., Milton, D. R., Dal, F., et al. (2016). Microsomal PGE2 synthase-1 regulates melanoma cell survival and associates with melanoma disease progression. Pigment Cell Melanoma Res. 29: 297-308.

Koeberle, A., and Werz, O. (2009). Inhibitors of the microsomal prostaglandin E(2) synthase-1 as alternative to non steroidal anti-inflammatory drugs (NSAIDs)—a critical review. Curr. Med. Chem. 16: 4274-96.

Koeberle, A., and Werz, O. (2015a). Perspective of microsomal prostaglandin E2 synthase-1 as drug target in inflammation-related disorders. Biochem. Pharmacol. 98: 1-15.

Koeberle, A., and Werz, O. (2015b). Perspective of microsomal prostaglandin E2 synthase-1 as drug target in inflammation-related disorders.

Kojima, F., Kato, S., and Kawai, S. (2005). Prostaglandin E synthase in the pathophysiology of arthritis. Fundam. Clin. Pharmacol. 19: 255-261.

Larsson, K., and Jakobsson, J. (2015). Inhibition of microsomal prostaglandin E synthase-1 as targeted therapy in cancer treatment. Prostaglandins Other Lipid Mediat. 120: 161-165.

Larsson, K., Kock, A., Idborg, H., Arsenian Henriksson, M., Martinsson, T., Johnsen, J. I., et al. COX/mPGES-1/PGE 2 pathway depicts an inflammatory-dependent high-risk neuroblastoma subset.

Mcadam, B. F., Catella-Lawson, F., Mardini, I. A., Kapoor, S., Lawson, J. A., and Fitzgerald, G. A. (1999). Systemic biosynthesis of prostacyclin by cyclooxygenase (COX)-2: The human pharmacology of a selective inhibitor of COX-2 (prostaglandinsplateletsmonocytesibuprofencelecoxib). Pharmacology 96: 272-277.

Miller, S. B. (2006). Prostaglandins in Health and Disease: An Overview. Semin. Arthritis Rheum. 36: 37-49.

Miyagishi, H., Kosuge, Y., Ishige, K., and Ito, Y. (2012). Expression of microsomal prostaglandin E synthase-1 in the spinal cord in a transgenic mouse model of amyotrophic lateral sclerosis. J. Pharmacol. Sci. 118: 225-36.

Nakanishi, M., Gokhale, V., Meuillet, E. J., and Rosenberg, D. W. (2010). mPGES-1 as a target for cancer suppression: A comprehensive invited review " Phospholipase A2 and lipid mediators". Biochimie 92: 660-4.

Nakanishi, M., and Rosenberg, D. W. (2013). Multifaceted roles of $PGE_2$ in inflammation and cancer. Semin. Immunopathol. 35: 123-137.

Norberg, J. K., Sells, E., Chang, H.-H., Alla, S. R., Zhang, S., and Meuillet, E. J. (2013a). Targeting inflammation: multiple innovative ways to reduce prostaglandin $E_2$. Pharm. Pat. Anal. 2: 265-88.

Norberg, J. K., Sells, E., Chang, H., Alla, S. R., Zhang, S., and Meuillet, E. J. (2013b). Targeting inflammation: multiple innovative ways to reduce prostaglandin $E_2$. Pharm. Pat. Anal. 2: 265-88.

Ramanan, M., and Doble, M. (2017). Transcriptional Regulation of mPGES1 in Cancer: An Alternative Approach to Drug Discovery? Curr. Drug Targets 18: 119-131.

Ricciotti, E., and FitzGerald, G. A. (2011). Prostaglandins and inflammation. Arterioscler. Thromb. Vasc. Biol. 31: 986-1000.

Riendeau, D., Aspiotis, R., Ethier, D., Gareau, Y., Grimm, E. L., Guay, J., et al. (2005). Inhibitors of the inducible microsomal prostaglandin E2 synthase (mPGES-1) derived from MK-886. Bioorg. Med. Chem. Lett. 15: 3352-3355.

Samuelsson, B., Morgenstern, R., and Jakobsson, P.-J. (2007). Membrane Prostaglandin E Synthase-1: A Novel Therapeutic Target. Pharmacol. Rev. Pharmacol Rev 59: 207-224.

Sasaki, Y., Nakatani, Y., and Hara, S. (2015). Role of microsomal prostaglandin E synthase-1 (mPGES-1)-derived prostaglandin E 2 in colon carcinogenesis. Prostaglandins Other Lipid Mediat. 121: 42-45.

Seo, T., Tatsuguchi, A., Shinji, S., Yonezawa, M., Mitsui, K., Tanaka, S., et al. Microsomal prostaglandin E synthase protein levels correlate with prognosis in colorectal cancer patients.

Smith, W. L., Urade, Y., and Jakobsson, P.-J. (2011). Enzymes of the Cyclooxygenase Pathways of Prostanoid Biosynthesis. 111: 5821-5865.

Takeuchi, C., Matsumoto, Y., Kohyama, K., Uematsu, S., Akira, S., Yamagata, K., et al. (2013). Microsomal prostaglandin E synthase-1 aggravates inflammation and demyelination in a mouse model of multiple sclerosis. Neurochem. Int. 62: 271-80.

Westman, M., Korotkova, M., Klint, E. af, Stark, A., Audoly, L. P., Klareskog, L., et al. (2004). Expression of microsomal prostaglandin E synthase 1 in rheumatoid arthritis synovium. Arthritis Rheum. 50: 1774-1780.

Yoshimatsu, K., Altorki, N. K., Golijanin, D., Zhang, F., Jakobsson, J., Dannenberg, A. J., et al. Inducible Prostaglandin E Synthase Is Overexpressed in Non-Small Cell Lung Cancer.

Zeilhofer, H. U. (2007). Prostanoids in nociception and pain. Biochem. Pharmacol. 73: 165-174.

---

The invention claimed is:

1. A method for treating a disease or condition mediated by enhanced mPGES-1 expression or activity, wherein the method comprises the step of administering to a subject suffering from the disease or condition an effective amount of a compound represented by general structure (I):

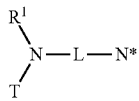
(I)

wherein,

T is represented by structure (IIIa) or (IIIb):

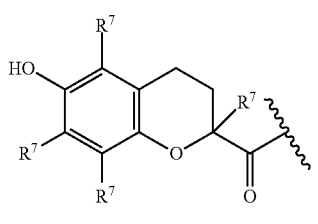
(IIIa)

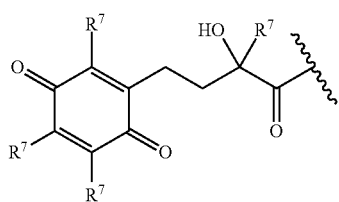
(IIIb)

wherein each $R^7$ is individually a $C_1$-$C_6$ alkyl moiety;

L is a linker selected from:
—$(CH_2)_2$—,
—$(CH_2)_2NHC(O)CH_2$—,
—$(CH_2)_3$—,
—$(CH_2)_2NHC(NH_2)$=,
—$(CH_2)_2NHC(O)CH_2NHC(NH_2)$=,
—$(CH_2)_3NHC(NH_2)$=,
—$(CH_2)_2NHC(Me)$=,
—$(CH_2)_2NHC(O)CH_2NHC(Me)$=,
—$(CH_2)_3NHC(Me)$=,
—$(CH_2)_2NR^{1'}C(NH_2)$=,
—$C(CO_2H)(CH_2)_3$—,
—$C(CO_2H)(CH_2)_3NHC(NH_2)$=,
—$C(CO_2H)CH_2$—,
—$C(CO_2H)(CH_2)_2$—,
—$C(CO_2H)(CH_2)_4$—,
—$(CH_2)_4$—,
—$(CH_2)_5$—,
—$CHR^{2'}C(O)$—,
—$CHR^{2'}CH_2$—,
—$CHR^5CH_2NR^{5'}C(Me)$=,
—$CHR^{2'}(CH_2)_2$—,
—$(CH_2)_2CHR^{1'}$—,
—$(CH_2)_2CHR^{1'}NHC(O)C(Me)$—,
—$CH_2CHR^{1'}$—,
—$CH_2CHR^{1'}NHC(Me)$=,
—$CHR^5(CH_2)_2CHR^{5'}$—,
—$CHR^{2'}CHR^{3'}(CH_2)_2$—, and
—$CR^5$=$CH$—$CH$=$CR^{5'}$—$CH_2$—, wherein $R^5$ and $R^{5'}$ represent the connection of a second linker between one backbone atom of the linker, bearing $R^5$, and another backbone atom of the linker, bearing $R^{5'}$, wherein $R^{5'}$ is joined with $R^5$ via the second linker, thus forming a 4-10-membered cyclic structure;

N* is represented by structure (IIa) or (IIb)

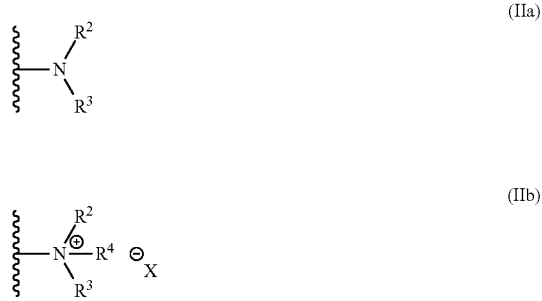

(IIa)

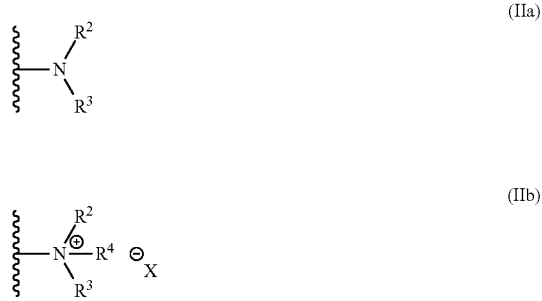

(IIb)

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with $R^{1'}$ of the linker L in a cyclic structure and/or $R^2$ is joined with $R^{2'}$ of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with $R^{3'}$ of the linker L in a cyclic structure; and $R^4$ is selected from hydrogen (H) or $C_1$-$C_6$ alkyl, wherein the alkyl moiety may be substituted with one or more halogen atoms or (halo)alkoxy moieties;

X is an anion, wherein the disease or condition is selected from the group consisting of: acute and chronic inflammation, dermatitis, eczema, psoriasis, burns, acne vulgaris, hidradenitis suppurativa, tissue trauma, inflammatory bowel disease, Crohn's disease, ulcerative colitis, diverticulitis, irritable bowel disease (IBS), peptic ulcers, cystitis, prostatitis, pancreatitis, nephritis, influenza, rhinitis, pharyngitis, tonsillitis, conjunctivitis, iritis, scleritis, otitis, uveitis, inflammation related anorexia, an allergy, pelvic inflammatory disease, reperfusion injury, transplant rejection, tendinitis, vasculitis, phlebitis, acute pain, chronic pain, neuropathic pain, nociceptive pain, hyperalgesia, pain related to central sensitization, allodynia inflammatory pain, visceral pain, cancer pain, trauma pain, dental or surgery pain, postoperative pain, delivery pain, childbirth ache, persistent pain, peripheral mediated pain, central mediated pain, chronic headache, migraine, sinus headaches, tension headaches, phantom limb pain, peripheral nerve injury chemotherapy pain, cancer pain, arthritis, juvenile arthritis, ankylosing spondylitis, gout, rheumatic fever, bursitis, systemic lupus erythematosus (SLE), multiple sclerosis, sarcoidosis, pulmonary fibrosis, brain cancer, prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma, skin B-cell lymphoma, diabetic vasculopathy, diabetic neuropathy, diabetic retinopathy, thrombosis, and coronary heart disease.

2. The method according to claim 1, wherein the compound is represented by structure (VI):

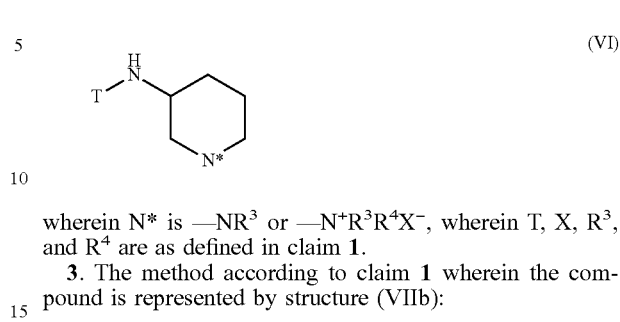

(VI)

wherein N* is —$NR^3$ or —$N^+R^3R^4X^-$, wherein T, X, $R^3$, and $R^4$ are as defined in claim 1.

3. The method according to claim 1 wherein the compound is represented by structure (VIIb):

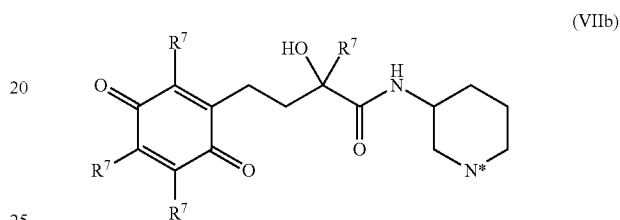

(VIIb)

wherein
each $R^7$ is methyl;
N* is —$NR^3$ or —$N^+R^3R^4X^-$;
X is as defined in claim 1;
$R^3$ is as defined in claim 1; and
$R^4$ is as defined in claim 1.

4. The method according to claim 1, wherein symptoms mediated by enhanced mPGES-1 expression or activity at least include one or more of inflammation, pain, swelling, fever, angiogenesis and anorexia.

5. The method according to claim 1, wherein the total daily dose that is administered is in the range of about 5 to 2000 mg.

6. The method according to claim 1, wherein the compound is administered orally.

7. The method according to claim 1, wherein the compound is administered at least twice daily.

8. The method according to claim 7, wherein the interval between two administrations is at least about 1, 2, 3, 4, 5, 6, 7, 8, 9, 10, 11 or 12 hours.

9. The method according to claim 1, wherein the subject to be treated is a primate.

10. The method according to claim 1, wherein $R^5$—$R^{5'}$ is —CH═CH—.

11. The method according to claim 1, wherein T is represented by structure (IVa) or (IVb), N* is represented by structure (IIa), or by structure (IIb) wherein $R^4$═H and X═Cl, and wherein:
(A) L═—$(CH_2)_2$—, $R^1$—$R^2$═—$(CH_2)_2$—, $R^3$═H;
(B) L═—$(CH_2)_2$—, $R^1$═H, $R^2$═H, $R^3$═H;
(C) L═—$(CH_2)_2NHC(O)CH_2$—, $R^1$═H, $R^2$═H, $R^3$═H;
(D) L═—$(CH_2)_3$—, $R^1$═H, $R^2$═H, $R^3$═H;
(E) L═—$(CH_2)_2NHC(NH_2)$═, $R^1$═H, $R^2$═H, $R^3$=absent;
(F) L═—$(CH_2)_2NHC(O)CH_2NHC(NH_2)$═, $R^1$═H, $R^2$═H, $R^3$=absent;
(G) L═—$(CH_2)_3NHC(NH_2)$═, $R^1$═H, $R^2$═H, $R^3$=absent;
(H) L═—$(CH_2)_3$—, $R^1$═H, $R^2$=Me, $R^3$=Me;
(I) L═—$(CH_2)_2$—, $R^1$═H, $R^2$=Me, $R^3$=Me;
(J) L═—$(CH_2)_2NHC(Me)$═, $R^1$═H, $R^2$═H, $R^3$=absent;
(K) L═—$(CH_2)_2NHC(O)CH_2NHC(Me)$═, $R^1$═H, $R^2$═H, $R^3$=absent;

(L) L=—(CH$_2$)$_3$NHC(Me)=, R$^1$=H, R$^2$=H, R$^3$=absent;
(M) L=—(CH$_2$)$_2$NR$^{1'}$C(NH$_2$)=, R$^1$—R$^{1'}$=—(CH$_2$)$_2$—, R$^2$=H, R$^3$=absent;
(N) L=—C(CO$_2$H)(CH$_2$)$_3$—, R$^1$=H, R$^2$=H, R$^3$=H;
(O) L=—C(CO$_2$H)(CH$_2$)$_3$NHC(NH$_2$)=, R$^1$=H, R$^2$=H, R$^3$=absent;
(P) L=—C(CO$_2$H)CH$_2$—, R$^1$=H, R$^2$=H, R$^3$=H;
(Q) L=—C(CO$_2$H)(CH$_2$)$_2$—, R$^1$=H, R$^2$=H, R$^3$=H;
(R) L=—C(CO$_2$H)(CH$_2$)$_4$—, R$^1$=H, R$^2$=H, R$^3$=H;
(S) L=—C(CO$_2$H)(CH$_2$)$_3$—, R$^1$=H, R$^2$=Me, R$^3$=Me
(T) L=—(CH$_2$)$_4$—, R$^1$=H, R$^2$=H, R$^3$=H;
(U) L=—(CH$_2$)$_5$—, R$^1$=H, R$^2$=H, R$^3$=H;
(V) L=—(CH$_2$)$_4$—, R$^1$=H, R$^2$=Me, R$^3$=Me;
(W) L=—CHR$^{2'}$C(O)—, R$^1$=H, R$^2$—R$^{1'}$=—(CH$_2$)$_3$—, R$^3$=H;
(X) L=CHR$^{1'}$CH$_2$, R$^1$=H, R$^2$—R$^{1'}$=—(CH$_2$)$_3$—, R$^3$=H;
(Y) L=—CHR$^5$CH$_2$NR$^{5'}$C(Me)=, R$^1$=H, R$^2$=H, R$^5$—R$^{5'}$=—(CH$_2$)$_3$—, R$^3$=absent;
(Z) L=—CHR$^{2'}$(CH$_2$)$_2$—, R$^1$=H, R$^2$—R$^{1'}$=—(CH$_2$)$_2$—, R$^3$=H;
(AA) L=—(CH$_2$)$_2$CHR$^{1'}$—, R$^1$—R$^{1'}$=—(CH$_2$)$_2$—, R$^2$=H, R$^3$=H;
(AB) L=—(CH$_2$)$_2$CHR$^{1'}$NHC(O)C(Me)-, R$^1$—R$^{1'}$=—(CH$_2$)$_2$—, R$^2$=H, R$^3$=H;
(AC) L=—CH$_2$CHR$^{1'}$—, R$^1$—R$^{1'}$=—(CH$_2$)$_3$—, R$^2$=H, R$^3$=H;
(AD) L=—CH$_2$CHR$^{1'}$NHC(Me)=, R$^1$—R$^{1'}$=—(CH$_2$)$_3$—, R$^2$=H, R$^3$=absent;
(AE) L=—CHR$^5$(CH$_2$)$_2$CHR$^{5'}$—, R$^1$=H, R$^2$=H, R$^5$—R$^{5'}$=—(CH$_2$)$_2$—, R$^3$=H;
(AF) L=CHR$^{2'}$CH$_2$, R$^1$=H, R$^2$—R$^{1'}$=—(CH$_2$)$_3$—, R$^3$=Me;
(AG) L=CHR$^{2'}$CH$_2$, R$^1$=H, R$^2$—R$^{1'}$=—(CH$_2$)$_2$—, R$^3$=H;
(AH) L=—CHR$^{2'}$(CH$_2$)$_2$—, R$^1$=H, R$^2$—R$^{1'}$=—(CH$_2$)$_2$—, R$^3$=Me;
(AI) L=—CHR$^{2'}$CHR$^{3'}$(CH$_2$)$_2$—, R$^1$=H, R$^2$—R$^{2'}$=—CH$_2$—, R$^3$—R$^{3'}$=—(CH$_2$)$_2$—, R$^4$=H, X=Cl; or
(AJ) L=—CR$^5$=CH—CH=CR$^{5'}$—CH$_2$—, R$^5$—R$^{5'}$ is —CH=CH—, R$^1$=H, R$^2$=H, R$^3$=H, R$^4$=H, X=Cl.

12. The method according to claim 1, wherein X is a pharmaceutically acceptable anion.
13. The method according to claim 1, wherein the compound is admixed with an aqueous solution or with an isotonic aqueous solution prior to administration.
14. The method according to claim 13, wherein the isotonic aqueous solution is saline.
15. The method according to claim 1, wherein the subject is human.
16. A method for inhibiting or suppressing functional activity of mPGES-1 in a subject, wherein the method comprises the step of administering to the subject an effective amount of a compound represented by general structure (I):

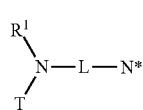
(I)

wherein,
T is represented by structure (IIIa) or (IIIb):

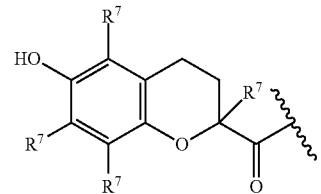
(IIIa)

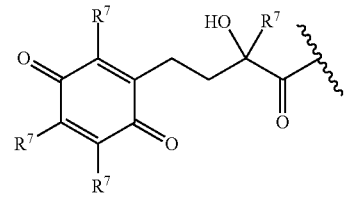
(IIIb)

wherein each R$^7$ is individually a C$_1$-C$_6$ alkyl moiety;
L is a linker selected from:
—(CH$_2$)$_2$—,
—(CH$_2$)$_2$NHC(O)CH$_2$—,
—(CH$_2$)$_3$—,
—(CH$_2$)$_2$NHC(NH$_2$)=,
—(CH$_2$)$_2$NHC(O)CH$_2$NHC(NH$_2$)=,
—(CH$_2$)$_3$NHC(NH$_2$)=,
—(CH$_2$)$_2$NHC(Me)=,
—(CH$_2$)$_2$NHC(O)CH$_2$NHC(Me)=,
—(CH$_2$)$_3$NHC(Me)=,
—(CH$_2$)$_2$NR$^{1'}$C(NH$_2$)=,
—C(CO$_2$H)(CH$_2$)$_3$—,
—C(CO$_2$H)(CH$_2$)$_3$NHC(NH$_2$)=,
—C(CO$_2$H)CH$_2$—,
—C(CO$_2$H)(CH$_2$)$_2$—,
—C(CO$_2$H)(CH$_2$)$_4$—,
—(CH$_2$)$_4$—,
—(CH$_2$)$_5$—,
—CHR$^{2'}$C(O)—,
—CHR$^{2'}$CH$_2$—,
—CHR$^5$CH$_2$NR$^{5'}$C(Me)=,
—CHR$^{2'}$(CH$_2$)$_2$—,
—(CH$_2$)$_2$CHR$^{1'}$—,
—(CH$_2$)$_2$CHR$^{1'}$NHC(O)C(Me)—,
—CH$_2$CHR$^{1'}$—,
—CH$_2$CHR$^{1'}$NHC(Me)=,
—CHR$^5$(CH$_2$)$_2$CHR$^{5'}$—,
—CHR$^{2'}$CHR$^{3'}$(CH$_2$)$_2$—, and
CR$^5$=CH—CH=CR$^{5'}$—CH$_2$—,
wherein R$^5$ and R$^{5'}$ represent the connection of a second linker between one backbone atom of the linker, bearing R$^5$, and another backbone atom of the linker, bearing R$^{5'}$, wherein R$^{5'}$ is joined with R$^5$ via the second linker, thus forming a 4-10-membered cyclic structure;
N* is represented by structure (IIa) or (IIb)

(IIa)

-continued

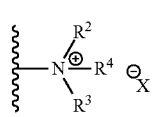
(IIb)

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with R" of the linker L in a cyclic structure and/or $R^2$ is joined with $R^{2'}$ of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with $R^{3'}$ of the linker L in a cyclic structure; and $R^4$ is selected from hydrogen (H) or $C_1$-$C_6$ alkyl, wherein the alkyl moiety may be substituted with one or more halogen atoms or (halo)alkoxy moieties;

X is an anion, wherein the subject has enhanced or increased activity of mPGES-1 as a result of overexpression of mPGES-1, wherein enhanced activity of mPGES-1 or overexpression of mPGES-1 is higher than in corresponding normal subjects.

17. The method according to claim 1, wherein the compound is an mPGES-1 inhibitor.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gattgtactc gcacgggcta c                                              21

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggataaggtt ggaccgcact                                                20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
```
aggactctgc tcacgaagga                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgacatggat tggaacagca                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
agcacactgc tggtcatcaa                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctccacatct gggtcactcc                                              20

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gctggggctg taccacac                                                18

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gattcacctc caccacctga                                              20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
ggtagagacc gccggagt                                                18

<210> SEQ ID NO 10
<211> LENGTH: 21
<212> TYPE: DNA
<213> ORGANISM: Artificial Sequence

```
<220> FEATURE:
<223> OTHER INFORMATION: Primer

<400> SEQUENCE: 10
tcgtaccact ttgcagaagc a                                    21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
agggtggtga ctttacacgc                                      20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gatgccagga cctgtatgct                                      20
```